(12) United States Patent
Sanai

(10) Patent No.: US 8,795,307 B2
(45) Date of Patent: Aug. 5, 2014

(54) ULTRASONIC TREATMENT DEVICE

(71) Applicant: Olympus Medical Systems Corp., Tokyo (JP)

(72) Inventor: Hideo Sanai, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/689,064

(22) Filed: Nov. 29, 2012

(65) Prior Publication Data

US 2013/0218185 A1  Aug. 22, 2013

Related U.S. Application Data

(63) Continuation of application No. PCT/JP2012/056281, filed on Mar. 12, 2012.

(60) Provisional application No. 61/468,293, filed on Mar. 28, 2011.

(51) Int. Cl.
*A61B 17/32* (2006.01)

(52) U.S. Cl.
USPC .......................................................... 606/169

(58) Field of Classification Search
CPC ............... A61B 17/320068; A61B 17/320092; A61B 2017/320072; A61B 2017/320088; A61B 2018/00607; A61B 2217/00; A61B 2217/002; A61B 2217/005; A61B 2217/007; A61B 2218/001; A61B 2218/002; A61B 2218/007; A61F 9/00745; A61N 7/00; A61N 7/02; A61N 7/022; A61N 2007/0043; A61N 2007/0047
USPC ........ 606/169, 27–28, 37; 600/437, 439, 459, 600/471; 604/22; 601/2; 607/96, 101
See application file for complete search history.

(56) References Cited

U.S. PATENT DOCUMENTS 4,886,491 A * 12/1989 Parisi et al. ...................... 604/22
5,312,327 A *  5/1994 Bales et al. ...................... 604/21
(Continued)

FOREIGN PATENT DOCUMENTS

EP     0 384 672 A2    8/1990
EP     2 591 734 A1    5/2013
(Continued)

OTHER PUBLICATIONS

International Search Report issued in International Patent Application No. PCT/JP2012/056281 mailed Apr. 17, 2012 (with translation).

(Continued)

*Primary Examiner* — Darwin Erezo
*Assistant Examiner* — Amy Shipley
(74) *Attorney, Agent, or Firm* — Oliff PLC

(57) ABSTRACT

An ultrasonic treatment device includes a probe in which a hole-shaped portion, being opened at a first opening position placed at a distal end portion of the probe and a second opening position placed at an outer peripheral portion of the probe and allowing the first opening position and the second opening position to communicate with each other, is formed. The ultrasonic treatment device includes a path which is extended in the hole-like portion from the first opening position to the second opening position along the longitudinal axis, and which is extended to an outside of the probe from the second opening position, and the path being extended to the extending position of the fixed handle toward the handle extending direction in the fixed handle.

8 Claims, 14 Drawing Sheets

(56) References Cited

U.S. PATENT DOCUMENTS

| | | | |
|---|---|---|---|
| 5,902,315 A * | 5/1999 | DuBois | 606/190 |
| 6,193,709 B1 * | 2/2001 | Miyawaki et al. | 606/1 |
| 6,200,311 B1 * | 3/2001 | Danek et al. | 606/15 |
| 6,558,376 B2 * | 5/2003 | Bishop | 606/27 |
| 6,666,860 B1 * | 12/2003 | Takahashi | 606/34 |
| 6,669,690 B1 * | 12/2003 | Okada et al. | 606/40 |
| 6,783,524 B2 * | 8/2004 | Anderson et al. | 606/28 |
| 6,893,434 B2 * | 5/2005 | Fenton et al. | 606/37 |
| 7,264,618 B2 * | 9/2007 | Murakami et al. | 606/27 |
| 7,572,257 B2 * | 8/2009 | Whayne et al. | 606/49 |
| 7,749,240 B2 * | 7/2010 | Takahashi et al. | 606/169 |
| 7,815,658 B2 * | 10/2010 | Murakami | 606/169 |
| 7,846,155 B2 * | 12/2010 | Houser et al. | 606/27 |
| 7,927,300 B2 * | 4/2011 | Tanaka | 604/22 |
| 8,034,053 B2 * | 10/2011 | Whayne et al. | 606/49 |
| 8,221,402 B2 * | 7/2012 | Francischelli et al. | 606/27 |
| 8,231,644 B2 * | 7/2012 | Onaga | 606/169 |
| 8,251,988 B2 * | 8/2012 | Takahashi | 606/34 |
| 8,353,907 B2 * | 1/2013 | Winkler et al. | 606/41 |
| 8,454,598 B2 * | 6/2013 | Whayne et al. | 606/49 |
| 8,663,220 B2 * | 3/2014 | Wiener et al. | 606/42 |
| 2002/0177843 A1 * | 11/2002 | Anderson et al. | 606/1 |
| 2002/0177846 A1 * | 11/2002 | Mulier et al. | 606/27 |
| 2003/0199794 A1 * | 10/2003 | Sakurai et al. | 601/2 |
| 2003/0225332 A1 * | 12/2003 | Okada et al. | 600/439 |
| 2004/0054364 A1 * | 3/2004 | Aranyi et al. | 606/27 |
| 2004/0097911 A1 * | 5/2004 | Murakami et al. | 606/27 |
| 2004/0133189 A1 * | 7/2004 | Sakurai | 606/1 |
| 2004/0186463 A1 * | 9/2004 | Murakami et al. | 606/27 |
| 2005/0021018 A1 * | 1/2005 | Anderson et al. | 606/28 |
| 2005/0021065 A1 * | 1/2005 | Yamada et al. | 606/169 |
| 2006/0265035 A1 * | 11/2006 | Yachi et al. | 607/101 |
| 2007/0043351 A1 * | 2/2007 | Fleischman et al. | 606/49 |
| 2007/0078452 A1 * | 4/2007 | Sekino | 606/27 |
| 2007/0198005 A1 * | 8/2007 | Ichihashi et al. | 606/27 |
| 2008/0058845 A1 * | 3/2008 | Shimizu et al. | 606/169 |
| 2008/0103498 A1 * | 5/2008 | West et al. | 606/41 |
| 2008/0114354 A1 * | 5/2008 | Whayne et al. | 606/49 |
| 2009/0036914 A1 * | 2/2009 | Houser | 606/169 |
| 2009/0054886 A1 * | 2/2009 | Yachi et al. | 606/27 |
| 2009/0270853 A1 * | 10/2009 | Yachi et al. | 606/27 |
| 2009/0270854 A1 * | 10/2009 | Yachi et al. | 606/27 |
| 2011/0066146 A1 * | 3/2011 | Jahns et al. | 606/33 |
| 2011/0118631 A1 * | 5/2011 | Onaga | 601/2 |
| 2011/0306972 A1 * | 12/2011 | Widenhouse et al. | 606/45 |
| 2012/0010539 A1 * | 1/2012 | Yachi et al. | 601/2 |
| 2012/0187806 A1 * | 7/2012 | Hirai et al. | 310/366 |
| 2013/0131705 A1 * | 5/2013 | Akagane | 606/169 |

FOREIGN PATENT DOCUMENTS

| | | |
|---|---|---|
| JP | U-63-65412 | 4/1988 |
| JP | A-7-16236 | 1/1995 |
| JP | A-11-146882 | 6/1999 |
| JP | A-2001-17445 | 1/2001 |
| JP | A-2006-223740 | 8/2006 |
| JP | A-2008-264565 | 11/2008 |
| WO | WO 00/22995 A2 | 4/2000 |

OTHER PUBLICATIONS

International Preliminary Report on Patentability mailed Oct. 11, 2013 issued in International Patent Application No. PCT/JP2012/056281.

Sep. 13, 2013 European Search Report Issued in European Application No. 12763619.9.

* cited by examiner

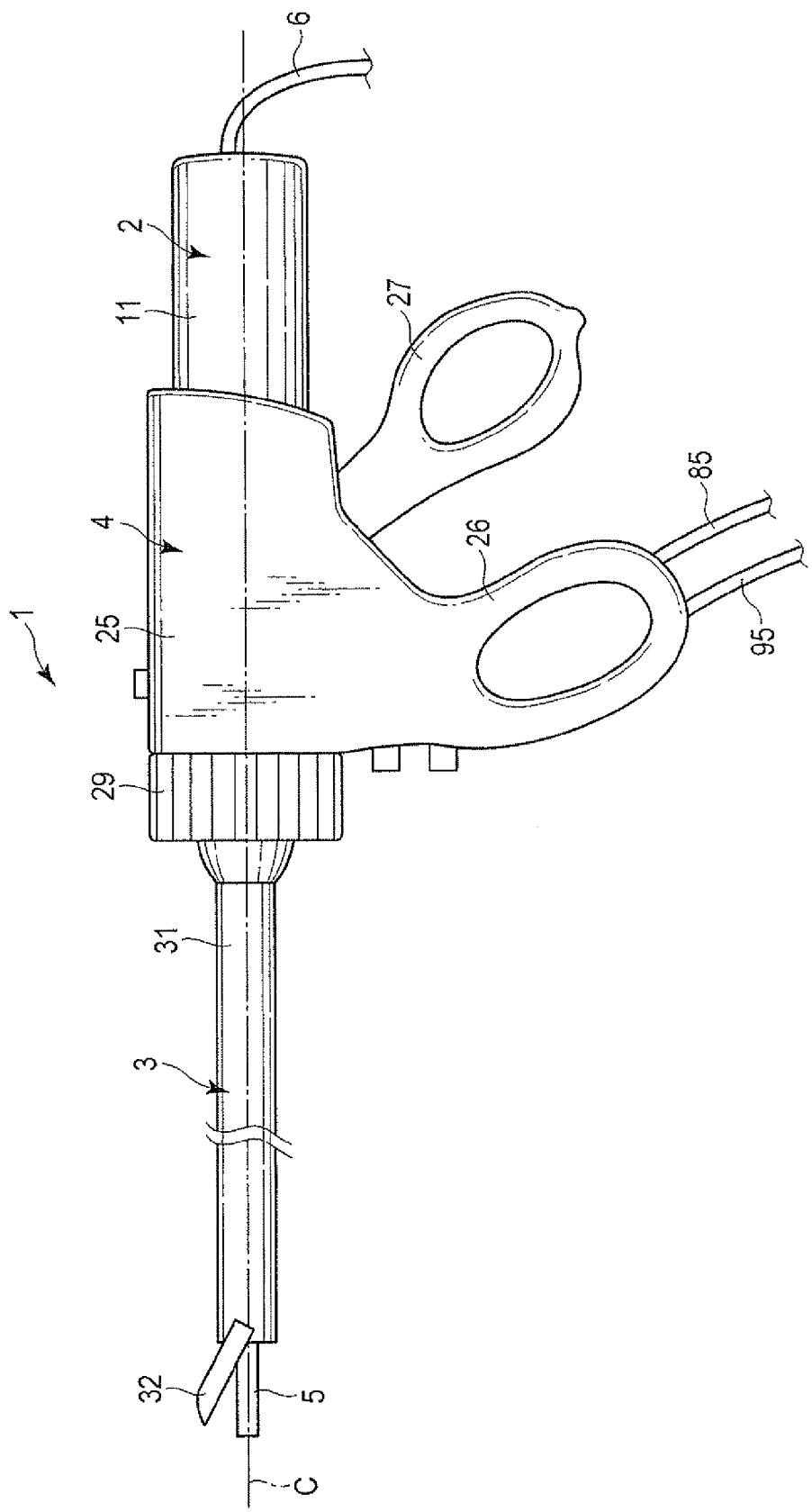
F I G. 13

ULTRASONIC TREATMENT DEVICE

CROSS-REFERENCE TO RELATED APPLICATIONS

This is a Continuation Application of PCT Application No. PCT/JP2012/056281, filed Mar. 12, 2012 and based upon and claiming the benefit of priority from prior U.S. Provisional Application No. 61/468,293, filed Mar. 28, 2011, the entire contents of which are incorporated herein by reference.

BACKGROUND OF THE INVENTION

1. Field of the Invention

The present invention relates to an ultrasonic treatment device (ultrasonic surgical apparatus) configured to perform an ultrasonic treatment (ultrasonic surgery) including ultrasonic suction and ultrasonic cutting-and-coagulation.

2. Description of the Related Art

Jpn. Pat. Appln. KOKAI Publication No. Hei 7-16236 discloses an ultrasonic suction device which includes an ultrasonic vibrator (ultrasonic oscillator), and a horn configured to transmit ultrasonic vibration generated by the ultrasonic vibrator from a proximal end to a distal end. In this ultrasonic suction device (ultrasonic aspiration device), an suction path is extended inside the horn along a longitudinal axis. The suction path (aspiration path) is bent at a bending position to a proximal direction side of the horn, and extended from the bending position toward an outer peripheral direction. Further, a suction pipe (aspiration pipe) is connected to the suction path on an outer peripheral portion of the ultrasonic vibrator. In this ultrasonic suction device, ultrasonic suction is conducted by a distal surface of the ultrasonically vibrating horn with using a physical phenomenon called "cavitation". In more detail, since the horn repeats fast vibration that is performed several tens of thousands of times per second based on the ultrasonic vibration, a pressure periodically varies near the distal surface of the horn. When the pressure near the distal surface is lower than a saturated vapor pressure for a short time due to a variation in pressure, small air bubbles (cavities) are produced in a liquid in a body cavity or a liquid supplied to a position near a treatment position (surgical target) of a body tissue from the ultrasonic treatment device. Furthermore, a force, which acts when the pressure near the distal surface is increased (compressed), annihilates the produced air bubbles. The above-described physical phenomenon is called a "cavitation phenomenon". A body tissue having no elasticity, like a liver cell, is shattered (crushed) and emulsified by impact energy at the time of annihilation of the air bubbles. The shattered and emulsified body tissue is suctioned (aspirated) and collected from a suction opening (aspiration opening) at the distal end of the horn through the suction path and an inside of the suction pipe. At this time, a body tissue having high elasticity, like a blood vessel, is difficult to shatter since it absorbs impact shock, and thereby body tissues are selectively shattered.

Jpn. Pat. Appln. KOKAI Publication No. 2008-264565 discloses an ultrasonic cutting-and-coagulation device including an ultrasonic vibrator (ultrasonic oscillator), and a non-hollow (columnar) probe configured to transmit ultrasonic vibration generated by the ultrasonic vibrator from a proximal end to a distal end. This ultrasonic cutting-and-coagulation device includes an elongated sheath into which the probe is inserted, and a jaw openable/closable with respect to a distal end portion of the probe. Moreover, the ultrasonic cutting-and-coagulation device includes a handle unit. In the handle unit, a treatment unit (surgery unit) including the probe, the sheath, and the jaw is coupled with a vibrator unit (oscillator unit) including the ultrasonic vibrator. The handle unit includes a fixed handle, and a movable handle openable/closable with respect to the fixed handle. When the movable handle is opened/closed with respect to the fixed handle, a movable portion, provided to the sheath, moves along the longitudinal axis. As a result, the jaw is opened/closed with respect to the distal end portion of the probe. An ultrasonic cutting-and-coagulation treatment (ultrasonic cutting-and-coagulation surgery) is carried out by utilizing the ultrasonic vibration while gripping a body tissue such as a blood vessel between the distal end portion of the probe and the jaw. Specifically, when the probe ultrasonically vibrates in a state that a body tissue such as a blood vessel is gripped between the distal end portion of the probe and the jaw, frictional heat is generated between the distal end portion of the probe and the body tissue. Cutting and coagulation of the body tissue are simultaneously performed between the distal end portion of the probe and the jaw by using the generated frictional heat. Further, in this ultrasonic cutting-and-coagulation device, the distal end portion of the probe and the jaw are used as electrodes, and a bipolar treatment (bipolar surgery) using a high-frequency current is also carried out.

BRIEF SUMMARY OF THE INVENTION

According to one aspect of the invention, an ultrasonic treatment device includes that a cylindrical case which is extended along a longitudinal axis; a fixed handle which is extended from the cylindrical case toward a handle extending direction that is a direction crossing the longitudinal axis; a movable handle which is pivotably attached to the cylindrical case, and which is openable/closable with respect to the fixed handle; a vibrator unit which includes an ultrasonic vibrator configured to generate ultrasonic vibration, and which is coupled to a proximal direction side of the cylindrical case; a probe in which a hole-shaped portion, being opened at a first opening position placed at a distal end portion of the probe and a second opening position placed at an outer peripheral portion of the probe and allowing the first opening position and the second opening position to communicate with each other, is formed, and which is configured to transmit the ultrasonic vibration generated by the ultrasonic vibrator from a proximal end to a distal end thereof; a jaw which is configured to open or close with respect to the distal end portion of the probe by opening or closing the movable handle with respect to the fixed handle; and a path which is extended in the hole-like portion from the first opening position to the second opening position along the longitudinal axis, and which is extended to an outside of the probe from the second opening position, and the path being extended to the extending position of the fixed handle toward the handle extending direction in the fixed handle.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general descrip

FIG. 13 is a schematic view showing an ultrasonic treatment device according to a first modification of the first embodiment;

DETAILED DESCRIPTION OF THE INVENTION

First Embodiment

Figure 1:
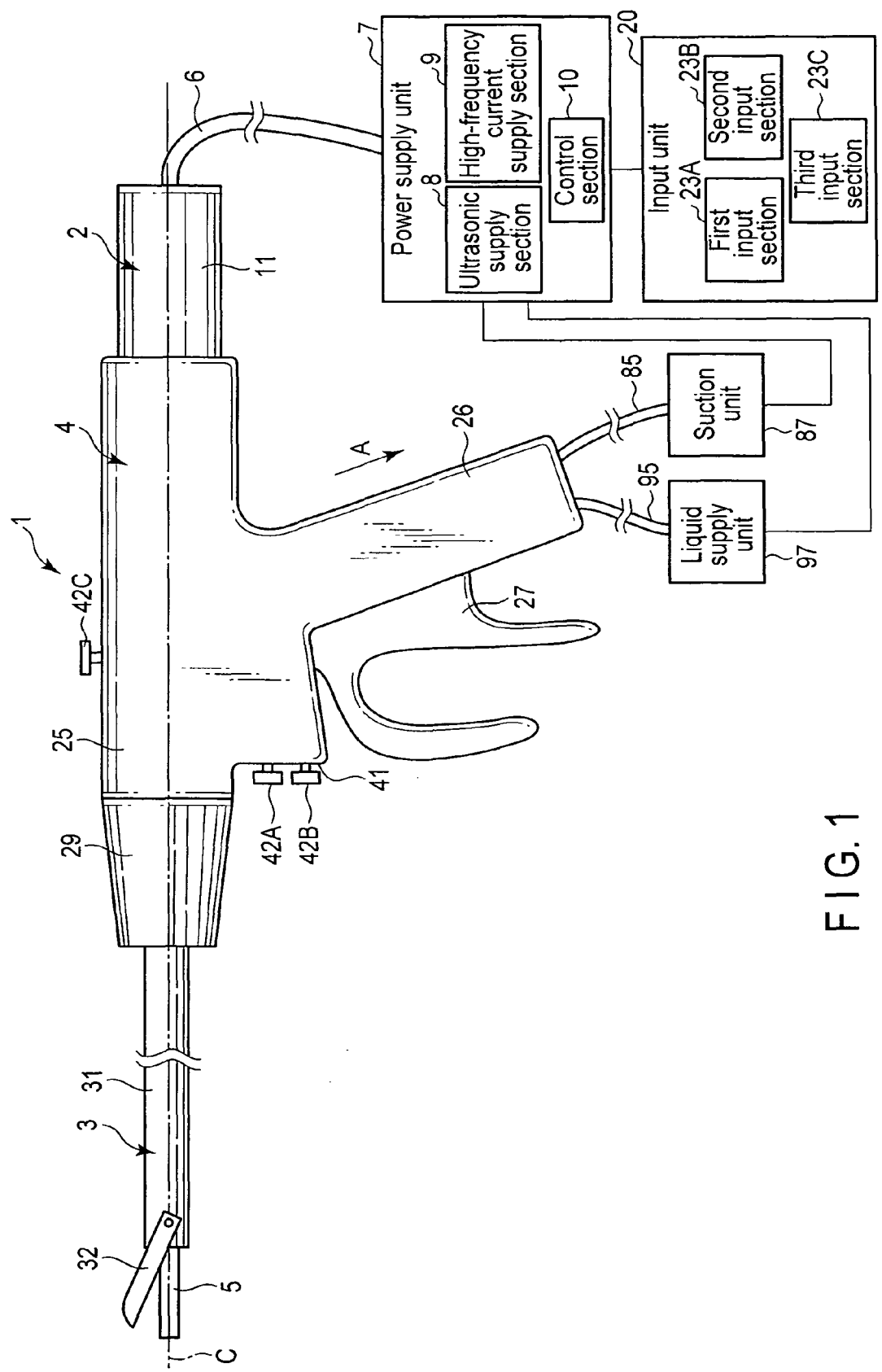
- FIG. 1 is a schematic view showing an ultrasonic treatment device according to a first embodiment of the present invention.

A first embodiment according to the present invention will now be described with reference to FIG. 1 to FIG. 12. FIG. 1 is a view showing an ultrasonic treatment device (ultrasonic surgical apparatus) 1 according to this embodiment. It is to be noted that the ultrasonic treatment device 1 according to this embodiment is an ultrasonic suction device (ultrasonic aspiration device) configured to selectively shatter (crush) and resect (excise) a body tissue by cavitation produced due to ultrasonic vibration and configured to suction (aspirate) the resected body tissue. Further, the ultrasonic treatment device 1 is also used as an ultrasonic cutting-and-coagulation device configured to carry out a cutting-and-coagulation treatment (cutting- and coagulation surgery) of a body tissue that is gripped between a distal end portion of a probe 5 (which will be described later) and a jaw 32 (which will be described later).

As shown in FIG. 1, the ultrasonic treatment device 1 includes a vibrator unit (oscillator unit) 2, a treatment unit (surgery unit) 3, and a handle unit 4. The treatment unit 3 includes a probe 5 that is extended along a longitudinal axis C.

The vibrator unit 2 includes a vibrator case (oscillator case) 11. One end of a cable is connected to a proximal end of the vibrator case 11. The other end of the cable 6 is connected to a power supply unit 7. The power supply unit 7 includes an ultrasonic supply section 8, a high-frequency current supply section 9, and a control section 10. An input unit 20 such as a foot switch is connected to the control section 10 of the power supply unit 7. The input unit 20 includes a first input section 23A, a second input section 23B, and a third input section 23C.

Figure 2:
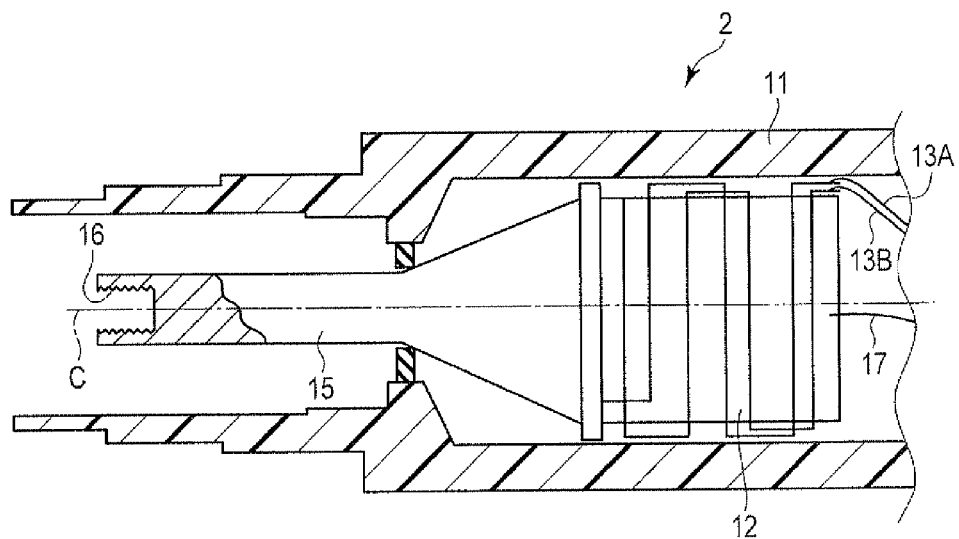
FIG. 2 is a cross-sectional view schematically showing a configuration of a vibrator unit according to the first embodiment.

FIG. 2 is a view showing a configuration of the vibrator unit 2. As shown in FIG. 2, an ultrasonic vibrator (ultrasonic oscillator) 12 including piezoelectric elements configured to convert an electric current into ultrasonic vibration is provided in the vibrator case 11. One end of each of electrical signal lines 13A and 13B is connected to the ultrasonic vibrator 12. The other end of each of the electrical signal lines 13A and 13B is connected to the ultrasonic supply section 8 in the power supply unit 7 through an inside of the cable 6. When the electric current is supplied to the ultrasonic vibrator 12 from the ultrasonic supply section 8 through the electrical signal lines 13A and 13B, ultrasonic vibration is produced in the ultrasonic vibrator 12. A horn 15 configured to increase an amplitude of the ultrasonic vibration is coupled to a distal direction side of the ultrasonic vibrator 12.

The horn 15 is attached to the vibrator case 11, and it is electrically insulated from the vibrator case 11. Furthermore, a female screw portion 16 is formed in a distal end portion of the horn 15. Moreover, an electrical signal line 17 extended from the high-frequency current supply section 9 in the power supply unit 7 through the inside of the cable 6 is connected to the ultrasonic vibrator 12 in addition to the electrical signal lines 13A and 13B.

Figure 3:
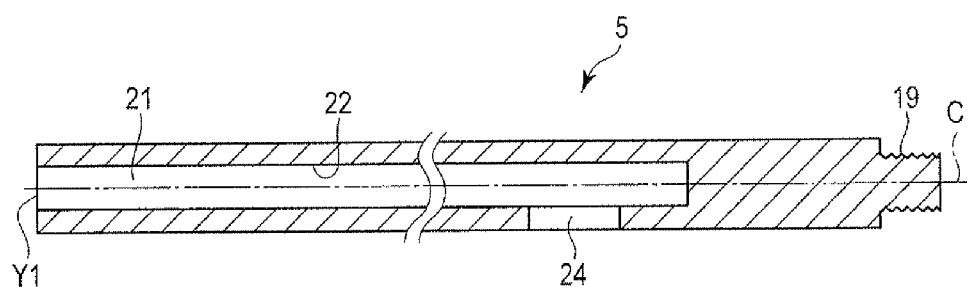
FIG. 3 is a cross-sectional view schematically showing a configuration of a probe according to the first embodiment.

FIG. 3 is a view showing a configuration of the probe 5. As shown in FIG. 3, a male screw portion 19 is provided at a proximal direction side portion of the probe 5. When the male screw portion 19 of the probe 5 is screwed into the female screw portion 16 of the horn 15, the probe 5 is attached to the horn 15.

When the probe 5 is attached to the horn 15, the ultrasonic vibration generated in the ultrasonic vibrator 12 is transmitted to a distal end of the probe 5 through the horn 15. That is, the ultrasonic vibration is transmitted from a proximal end to the distal end of the probe 5. It is to be noted that the ultrasonic vibration is longitudinal vibration, in which a vibration transmission direction coincides with a vibration direction.

Additionally, when the probe 5 is attached to the horn 15, a probe-side current path of the high-frequency current is formed from the high-frequency current supply section 9 to a distal end portion of the probe 5 through the electrical signal line 17, the ultrasonic vibrator 12, and the horn 15. The probe-side current path is configured to transmit the high-frequency current between the high-frequency current supply section 9 and the distal end portion of the probe 5 along the longitudinal axis C.

A hole-shaped portion 21 is extended in the probe 5 from the distal end portion of the probe 5 along the longitudinal axis C. The hole-shaped portion 21 is opened at an opening position Y1 located at the distal end portion of the probe 5. The hole-shaped portion 21 is defined by a hole defining surface 22 of the probe 5. A proximal end of the hole-shaped portion 21 is placed to the distal direction side of the proximal end of the probe 5. Therefore, a proximal direction side portion of the probe 5 is formed into a columnar shape (non-hollow). Additionally, in the probe 5, an opening hole 24 extended from an outer peripheral portion to the proximal end portion of the hole-shaped portion 21 in radial directions is provided.

As shown in FIG. 1, the handle unit 4 includes a cylindrical case 25 extended along the longitudinal axis C. The cylindrical case 25 is made of an insulating material. A fixed handle 26 is extended from the cylindrical case 25 toward a handle extending direction (a direction of an arrow A in FIG. 1) that is not parallel to the longitudinal axis C. In this embodiment, the fixed handle 26 is provided to be inclined with respect to the longitudinal axis C. Further, a movable handle 27 is pivotably attached to the cylindrical case 25. The movable handle 27 is be openable and closable with respect to the fixed handle 26 substantially in parallel with the longitudinal axis C. The movable handle 27 is placed to the distal direction side of the fixed handle 26.

The vibrator unit 2 is coupled with the cylindrical case 25 from the proximal direction side. Moreover, the treatment unit 3 is coupled with the cylindrical case 25 from the distal direction side. The treatment unit 3 includes a sheath portion 31 into which the probe 5 is inserted so that the probe 5 protrudes in the distal direction, and a jaw 32 which is pivotably attached to a distal end portion of the sheath portion 31. The jaw 32 is openable/closable with respect to the distal end portion of the probe 5. In a state that the treatment unit 3 is coupled with the cylindrical case 25, a distal end of the sheath portion 31 is placed to the distal direction side of a distal end of the handle unit 4. Therefore, in a state that the treatment unit 3 is coupled with the cylindrical case 25, the probe 5 is extended to a part to the distal direction side of the distal end of the handle unit 4 along the longitudinal axis C.

Moreover, the handle unit 4 includes a rotating operation knob 29, which is a rotating operation section, coupled to the distal direction side of the cylindrical case 25. The rotating operation knob 29 is coupled with the cylindrical case 25 to be rotatable in periaxial directions. When the rotating operation knob 29 rotates with respect to the cylindrical case 25, the treatment unit 3 (the probe 5, the sheath portion 31, and the jaw 32) rotates in one of the periaxial directions with respect to the cylindrical case 25.

Figure 4:
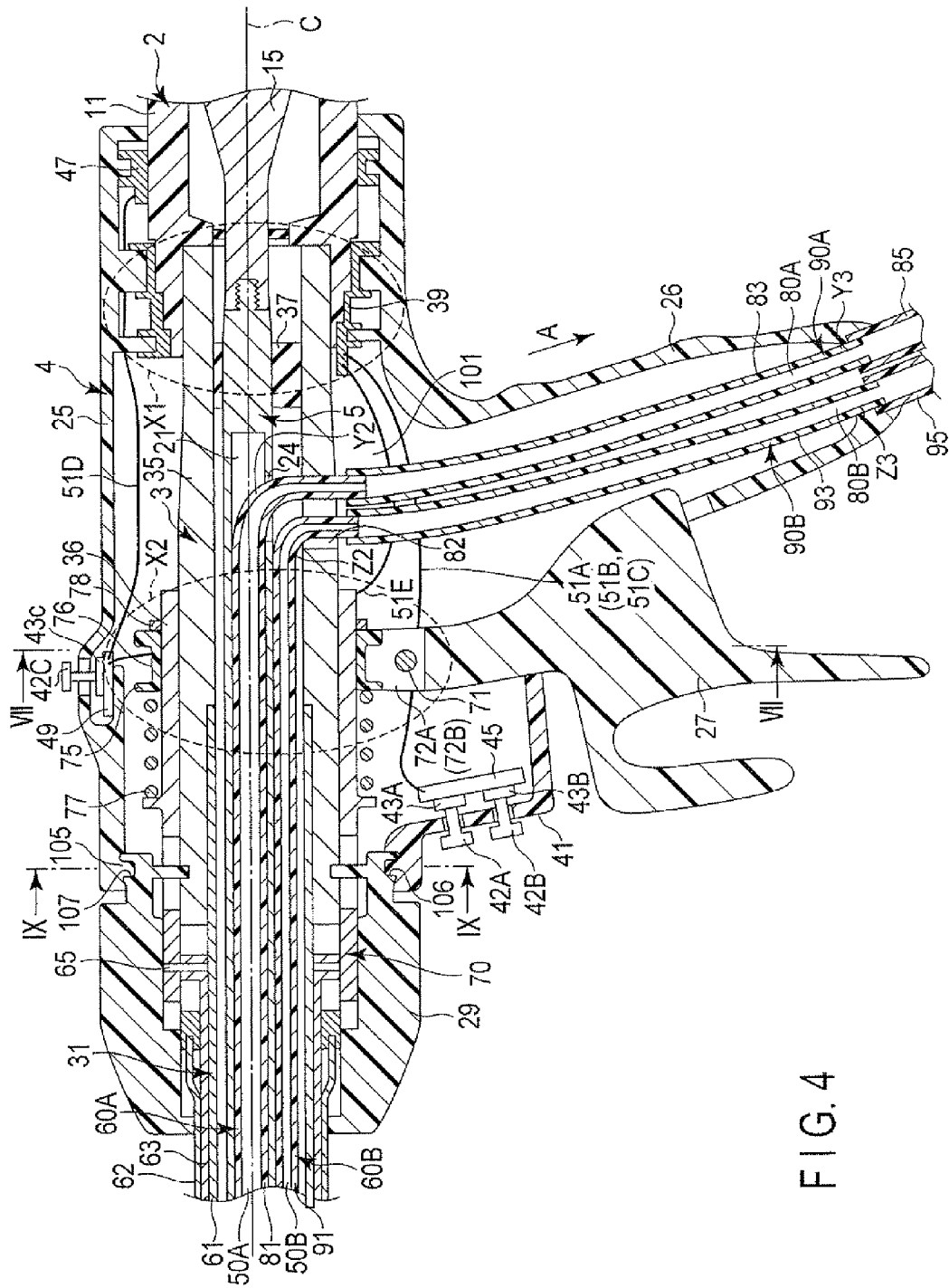
FIG. 4 is a cross-sectional view schematically showing an internal configuration of a handle unit according to the first embodiment.

FIG. 4 is a view showing a configuration of an inside of the handle unit 4. As shown in FIG. 4, the probe 5 and the sheath portion 31 are extended to an inside of the cylindrical case 25 through an inside of the rotating operation knob 29 along the longitudinal axis C. In a first coupling region X1 in the cylindrical case 25, the proximal end of the probe 5 is attached to the horn 15. That is, the probe 5 is extended from the first coupling region X1 in the cylindrical case 25 toward the distal direction. Furthermore, in the first coupling region X1 in the cylindrical case 25, a proximal end portion of the sheath portion 31 is coupled with the vibrator case 11. As described above, in the first coupling region X1 in the cylindrical case 25, the treatment unit 3 is coupled with the vibrator unit 2.

The sheath portion 31 includes a fixed cylindrical member 35 and a movable cylindrical member 36 which are coupled with the rotating operation knob 29. The fixed cylindrical member 35 and the movable cylindrical member 36 are provided along the longitudinal axis C. The fixed cylindrical member 35 is provided in a fixed state with respect to the rotating operation knob 29. The movable cylindrical member 36 is provided to be movable along the longitudinal axis C with respect to the rotating operation knob 29 and the fixed cylindrical member 35. Moreover, the movable cylindrical member 36 is regulated so that it does not move in the periaxial directions with respect to the rotating operation knob 29. With the above-described configuration, the fixed cylindrical member 35 and the movable cylindrical member 36 rotate integrally with the rotating operation knob 29 in the periaxial directions with respect to the cylindrical case 25. Additionally, the movable cylindrical member 36 can move along the longitudinal axis C with respect to the handle unit 4 and the probe 5.

A proximal end of the fixed cylindrical member 35 is extended to the first coupling region X1. The probe 5 is supported by the fixed cylindrical member 35 through an insulating member 37. As a result, the probe 5 is prevented from coming into contact with the fixed cylindrical member 35, and the probe 5 is electrically insulated from the fixed cylindrical member 35 (the sheath portion 31). Further, the probe 5 is fixed to the fixed cylindrical member 35 by using the insulating member 37. As a result, a rotary drive force of the rotating operation knob 29 is transmitted to the probe 5 through the fixed cylindrical member 35. Therefore, the probe 5 can rotate with respect to the cylindrical case 25 integrally with the rotating operation knob 29 and the fixed cylindrical member 35.

In the first coupling region X1, an electrical connection ring 39 is provided to an outer peripheral direction side of the fixed cylindrical member 35. The electrical connection ring 39 is provided in a fixed state with respect to the cylindrical case 25. Furthermore, a distal end portion of the vibrator case 11 is engaged between the fixed cylindrical member 35 and the electrical connection ring 39. When the distal end portion of the vibrator case 11 is engaged between the fixed cylindrical member 35 and the electrical connection ring 39, the vibrator case 11 is coupled with the sheath portion 31 (the fixed cylindrical member 35). In a state that the vibrator case 11 is coupled with the sheath portion 31, an outer peripheral portion of the distal end portion of the vibrator case 11 is in contact with the electrical connection ring 39, and an inner peripheral portion of the distal end portion of the vibrator case 11 is in contact with the fixed cylindrical member 35.

The cylindrical case 25 includes a planar portion 41 that is substantially parallel to a handle extending direction (a direction of an arrow A in each of FIG. 1 and FIG. 4). The planar portion 41 is provided on the side where the fixed handle 26 and the movable handle 27 are placed with the longitudinal axis C being at the center. Further, the planar portion 41 is placed to the distal direction side of the movable handle 27.

Input buttons 42A and 42B as operation input sections are provided on the planar portion 41. When the respective input buttons 42A and 42B are pressed, an operation of an operator (surgeon) is input. To the proximal direction side of the planar portion 41, switch portions 43A and 43B and an electrical circuit board 45 are provided. ON/OFF states of the switch portion 43A are changed over by an input operation using the input button 42A. Likewise, ON/OFF states of the switch portion 43B are changed over by an input operation using the input button 42B.

To the proximal direction side of the first coupling region X1, an electrical connection ring 47 is provided in a fixed state with respect to the cylindrical case 25. The electrical connection ring 47 is placed to the outer peripheral direction side of the vibrator case 11. In a state that the vibrator case 11 is coupled with the sheath portion 31, the electrical connection ring 47 is in contact with the outer peripheral portion of the vibrator case 11.

An input button 42C, which is an operation input section, is provided on an outer peripheral portion of the cylindrical case 25. The input button 42C is provided on an opposite side of the side where the fixed handle 26 and the movable handle 27 are placed with the longitudinal axis C being at the center. When the input button 42C is pressed, an operation of an operator (surgeon) is input. To an inner peripheral direction side of the input button 42C, a switch portion 43C and an electrical circuit board 49 are provided. ON/OFF states of the switch portion 43C are changed over by an input operation using the input button 42C.

Figure 5:
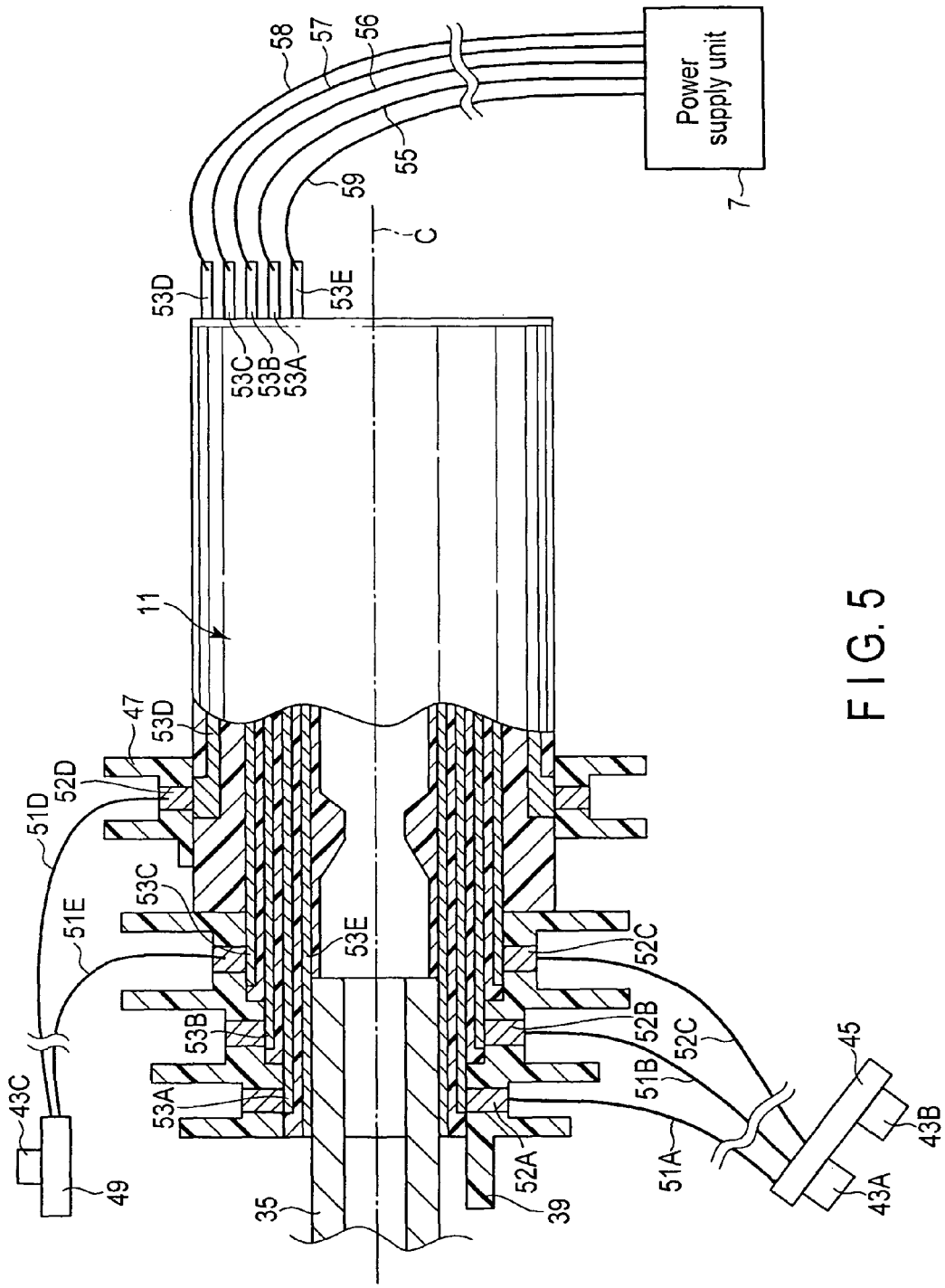
FIG. 5 is a schematic view showing a state of electrical connection in the vibrator case according to the first embodiment.

FIG. 5 is a view schematically showing an electrical connection state in the vibrator case 11. As shown in FIG. 4 and FIG. 5, in the cylindrical case 25, five electrical signal lines 51A to 51E are provided. The electrical signal line 51A is electrically connected to the switch portion 43A through the electrical circuit board 45. The electrical signal line 51B is electrically connected to the switch portion 43B through the electrical circuit board 45. The electrical signal line 51C is electrically connected to the switch portion 43A and the switch portion 43B through the electrical circuit board 45. The electrical signal line 51C is a common line shared as a ground line of the switch portion 43A and the switch portion 43B. The electrical signal lines 51D and 51E are connected to the switch portion 43C. The electrical signal line 51E is used as a ground line of the switch portion 43C.

The electrical connection ring 39 includes a first electrical connecting portion 52A, a second electrical connecting portion 52B, and a third electrical connecting portion 52C. The first electrical connecting portion 52A is electrically insulated from the second electrical connecting portion 52B, the second electrical connecting portion 52B is electrically connected from the third electrical connecting portion 52C, and the first electrical connecting portion 52A is electrically insulated from the third electrical connecting portion 52C. The electrical signal line 51A is connected to the first electrical connecting portion 52A. The electrical signal line 51B is connected to the second electrical connecting portion 52B. The electrical signal line 51C is connected to the third electrical connecting portion 52C. Furthermore, the electrical connection ring 47 includes a fourth electrical connecting portion 52D. The electrical signal line 51D is connected to the fourth electrical connecting portion 52D. The electrical signal line 51E is connected to the third electrical connecting portion 52C.

Moreover, the vibrator case 11 includes a first conductive portion 53A, a second conductive portion 53B, and a third conductive portion 53C. The first conductive portion 53A, the second conductive portion 53B, and the third conductive portion 53C are extended along the longitudinal axis C. The first conductive portion 53A is electrically insulated from the second conductive portion 53B, the second conductive portion 53B is electrically insulated from the third conductive portion 53C, and the first conductive portion 53A is electrically insulated from the third conductive portion 53C. In a state that the vibrator case 11 is coupled with the sheath portion 31, a distal end portion of the first conductive portion 53A alone is electrically in contact with the first electrical connecting portion 52A of the electrical connection ring 39. Likewise, a distal end portion of the second conductive portion 53B alone is electrically in contact with the second electrical connecting portion 52B of the electrical connection ring 39. Further, a distal end portion of the third conductive portion 53C alone is electrically in contact with the third electrical connecting portion 52C of the electrical connection ring 39. Furthermore, the vibrator case 11 includes a fourth conductive portion 53D extended along the longitudinal axis C. The first conductive portion 53A, the second conducive portion 53B, and the third conductive portion 53C are all electrically insulated from the fourth conductive portion 53D. In a state that the vibrator case 11 is coupled with the sheath portion 31, a distal end portion of the fourth conductive portion 53D alone is electrically in contact with the fourth electrical connecting portion 52D of the electrical connection ring 47.

One end of an electrical signal line 55 is connected to a proximal end portion of the first conductive portion 53A. One end of an electrical signal line 56 is connected to a proximal end portion of the second conductive portion 53B. One end of an electrical signal line 57 is connected to a proximal end portion of the third conductive portion 53C. One end of an electrical signal line 58 is connected to a proximal end portion of the fourth conductive portion 53D. The other end of each of the electrical signal lines 55 to 58 is connected to the control section 10 in the power supply unit 7 through the inside of the cable 6.

As described above, there is formed a first electrical signal path extending from the switch portion 43A to the control section 10 in the power supply unit 7 through the electrical signal line 51A, the first electrical connecting portion 52A, the first conductive portion 53A, and the electrical signal line 55. Further, there is formed a second electrical signal path extending from the switch portion 43B to the control section 10 in the power supply unit 7 through the electrical signal line 51B, the second electrical connecting portion 52B, the second conductive portion 53B, and the electrical signal line 56. Furthermore, there is formed a first ground path extending from the switch portion 43A and the switch portion 43B to the control section 10 through the electrical signal line 51C, the third electrical connecting portion 52C, the third conductive portion 53C, and the electrical signal line 57. Additionally, there is formed a third electrical signal path extending from the switch portion 43C to the control section 10 through the electrical signal line 51D, the fourth electrical connecting portion 52D, the fourth conductive portion 53D, and the electrical signal line 58. Further, there is formed a second ground path extending from the switch portion 43C to the control section 10 through the electrical signal line 51E, the third electrical connecting portion 52C, the third conducive portion 53C, and the electrical signal line 57. The third electrical connecting portion 52C, the third conductive portion 53C, and the electrical signal line 57 are shared as the first ground path and the second ground path.

When the input button 42A is pressed, the switch portion 43A is closed, and the switch portion 43A enables electrically connecting the first electrical signal path to the first ground path. As a result, an electrical signal is transmitted from the switch portion 43A to the control section 10 in the power supply unit 7. Furthermore, when the input button 42B is pressed, the switch portion 43B is closed, and the switch portion 43B enables electrically connecting the second electrical signal path to the first ground path. As a result, an electrical signal is transmitted from the switch portion 43B to the control section 10 in the power supply unit 7. Moreover, when the input button 42C is pressed, the switch portion 43C is closed, and the switch portion 43C enables electrically connecting the third electrical signal path to the second ground path. As a result, an electrical signal is transmitted from the switch portion 43C to the control section 10 in the power supply unit 7.

As shown in FIG. 5, the vibrator case 11 includes a fifth conductive portion 53E extended along the longitudinal axis C. All of the first conductive portion 53A, the second conductive portion 53B, the third conductive portion 53C, and the fourth conductive portion 53D are electrically insulated from the fifth conductive portion 53E. An electrical signal line 59 extended from the high-frequency current supply section 9 in the power supply unit 7 through the inside of the cable 6 is connected to a proximal end portion of the fifth conductive portion 53E. In a state that the vibrator case 11 is coupled with the sheath portion 31, a distal end portion of the fifth conductive portion 53E alone is electrically in contact with the fixed cylindrical member 35. As described above, a high-frequency current is transmitted between the high-frequency current supply section 9 and the fixed cylindrical member 35 of the sheath portion 31 through the electrical signal line 59 and the fifth conducive portion 53E.

As shown in FIG. 4, the sheath portion 31 includes an inner pipe 61 and an outer pipe 62 coupled with the distal end portion of the fixed cylindrical member 35. The inner pipe 61 and the outer pipe 62 are provided in a fixed state with respect to the fixed cylindrical member 35. An outer peripheral portion of the outer pipe 62 is subjected to an insulative coating treatment. Further, the sheath portion 31 includes a movable pipe 63 provided between the inner pipe 61 and the outer pipe 62. The movable pipe 63 is fixed to the distal end portion of the movable cylindrical member 36 through a connection pin 65. The movable pipe 63 is movable with respect to the inner pipe 61 and the outer pipe 62 integrally with the movable cylindrical member 36. That is, the movable pipe 63 is movable with respect to the handle unit 4 and the probe 5 integrally with the movable cylindrical member 36 along the longitudinal axis C. Furthermore, the inner pipe 61, the outer pipe 62, and the movable pipe 63 rotate in the periaxial directions with respect to the cylindrical case 25 integrally with the rotating operation knob 29. Moreover, a high-frequency current is transmitted between the fixed cylindrical member 35 and the movable pipe 63 through the movable cylindrical member 36 and the connection pin 65.

Figure 6:
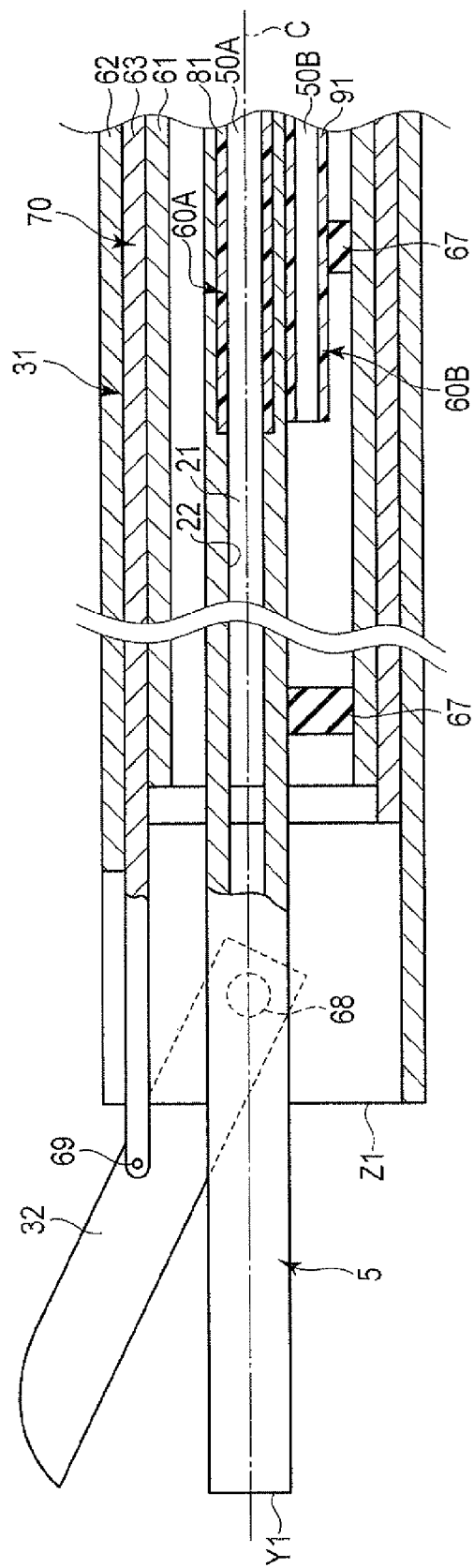
FIG. 6 is a cross-sectional view schematically showing a state that the probe is inserted through a sheath portion according to the first embodiment.

FIG. 6 is a view showing a state that the probe 5 is inserted through the sheath portion 31. As shown in FIG. 6, the inner pipe 61, the outer pipe 62, and the movable pipe 63 are extended to the distal end portion of the sheath portion 31 along the longitudinal axis C. A support member 67 is provided between the probe 5 and the inner pipe 61 (the sheath portion 31). The support member 67 is made of an insulating material. The support member 67 prevents the probe 5 from coming into contact with the inner pipe 61, and achieves electrical insulation between the probe 5 and the sheath portion 31 (the movable pipe 63). The support member 67 is arranged at a node position of the ultrasonic vibration. As a result, contact between the probe 5 and the inner pipe 61 is further effectively avoided. Additionally, when the insulative coating treatment is performed with respect to an inner peripheral portion of the inner pipe 61, the probe 5 and the sheath portion 31 are more effectively insulated from each other.

The jaw 32 is attached to a distal end portion of the outer pipe 62 through a coupling screw 68. The jaw 32 pivots about the coupling screw 68 with respect to the sheath portion 31. Further, a distal end portion of the movable pipe 63 is coupled with the jaw 32 through a connection pin 69. A high-frequency current is transmitted between the movable pipe 63 and the jaw 32 through the connection pin 69. As described above, there is formed a jaw-side current path extending from the high-frequency current supply section 9 to the jaw 32 through the electrical signal line 59, the fifth conductive portion 53E, the fixed cylindrical member 35, the movable cylindrical member 36, and the movable pipe 63. The jaw-side current path enables transmission of the high-frequency current between the high-frequency current supply section 9 and the jaw 32.

Figure 7:
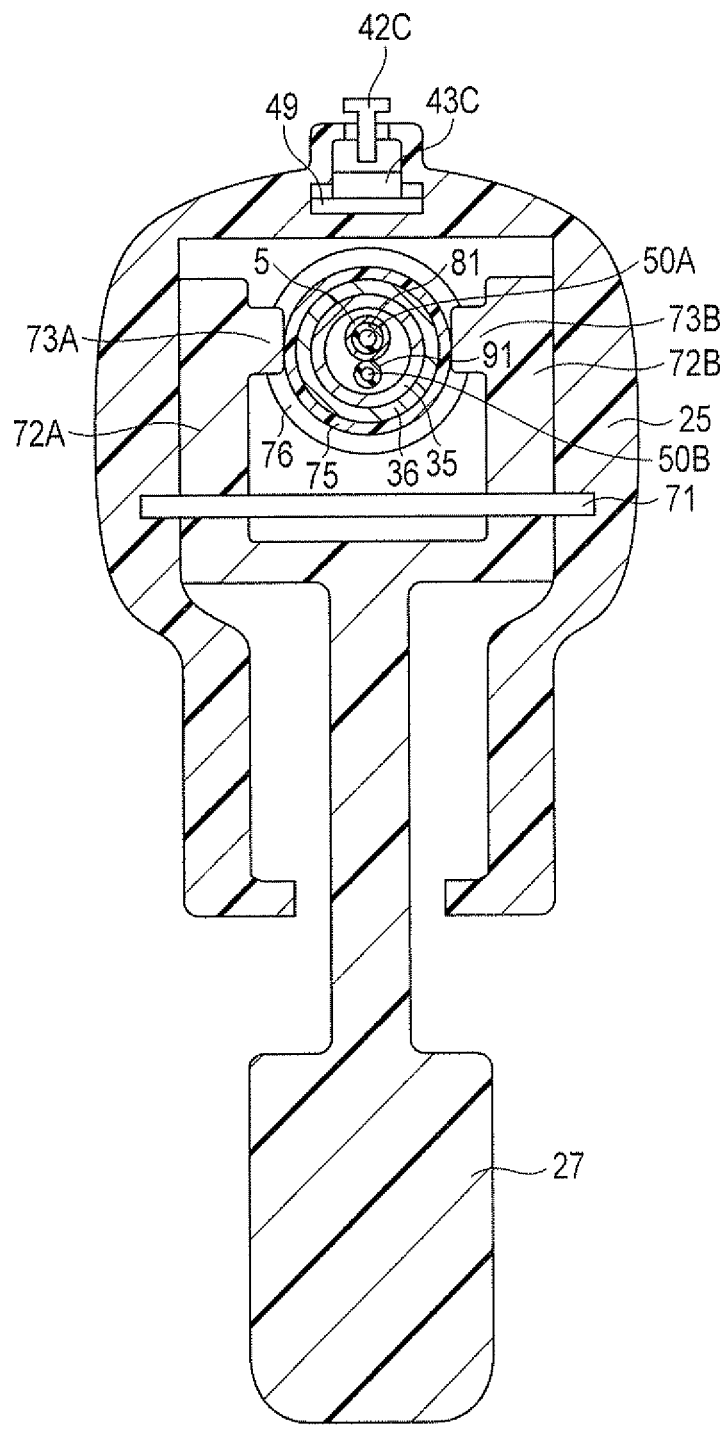
FIG. 7 is a cross-sectional view taken along a line VII-VII in FIG. 4.

FIG. 7 is a cross-sectional view taken along a line VII-VIII in FIG. 4. As shown in FIG. 4 and FIG. 7, the movable handle 27 is attached to the cylindrical case 25 through a fulcrum pin 71. The movable handle 27 pivots with respect to the cylindrical case 25 about the fulcrum pin 71 at the center. Further, the movable handle 27 includes arm portions 72A and 72B. An engagement protrusion 73A protruding toward an inner peripheral direction is provided to the arm portion 72A, and an engagement protrusion 73B protruding toward the inner peripheral direction is provided to the arm portion 72B.

A slide member 75 is arranged to the outer peripheral direction side of the movable cylindrical member 36. An engagement groove 76, which is concave toward the inner peripheral direction, is formed on the slide member 75 along the periaxial directions. When the engagement protrusions 73A and 73B engage with the engagement groove 76, the movable handle 27 is attached to the slide member 75. The slide member 75 is provided in a second coupling region X2 in the cylindrical case 25, the second coupling region X2 being placed to the distal direction side of the first coupling region X1. Therefore, the movable handle 27 is attached to the slide member 75 in the second coupling region X2 in the cylindrical case 25. Further, the slide member 75 is made of an insulating material. Therefore, the movable cylindrical member 36 (the sheath portion 31) is electrically insulated from the movable handle 27.

Furthermore, a coil spring 77 and a stopper 78 are provided to the outer peripheral direction side of the movable cylindrical member 36. One end of the coil spring 77 is connected to a distal end of the slide member 75, and the other end of the same is connected to the movable cylindrical member 36. Moreover, the stopper 78 is configured to regulate movement of the slide member 75 toward the proximal direction.

When the movable handle 27 is opened or closed with respect to the fixed handle 26 and the movable handle 27 thereby pivots about the fulcrum pin 71, the slide member 75 moves with respect to the movable cylindrical member 36 along the longitudinal axis C. Moreover, when a force, which is not smaller than a predetermined force, is applied to the movable cylindrical member 36 from the slide member 75 through the coil spring 77, the movable cylindrical member 36 moves with respect to the handle unit 4 and the probe 5 along the longitudinal axis C integrally with the slide member 75. When the movable cylindrical member 36 moves, the movable pipe 63 moves along the longitudinal axis C integrally with the movable cylindrical member 36. Additionally, the jaw 32 opens or closes with respect to the distal end portion of the probe 5.

As described above, the slide member 75, the movable cylindrical member 36, and the movable pipe 63 serve as a movable portion 70 which moves with respect to the handle unit 4 and the probe 5 along the longitudinal axis C in accordance with the opening/closing motions of the movable handle 27 with respect to the fixed handle 26. The movable portion 70 is coupled with the movable handle 27 in the second coupling region X2 in the cylindrical case 25, the second coupling portion X2 being placed to the distal direction side of the first coupling region X1. When the movable portion 70 moves along the longitudinal axis C, the jaw 32 opens or closes with respect to the distal end portion of the probe 5.

As shown in FIG. 4 and FIG. 6, in the hole-shaped portion 21 in the probe 5, a first suction tube member (a first tube member) 81 is extended along the longitudinal axis C. The first suction tube member (first aspiration tube member) 81 is extended to a bending position Y2 provided between the first coupling region X1 and the second coupling region X2. That is, the bending position Y2 is provided to the distal direction side of the first coupling region X1, and also provided to the proximal direction side of the second coupling region X2. It is to be noted that the hole-shaped portion 21 is extended to a region positioned to the proximal direction side of the bending position Y2 of the first suction tube member 81.

Figure 8:
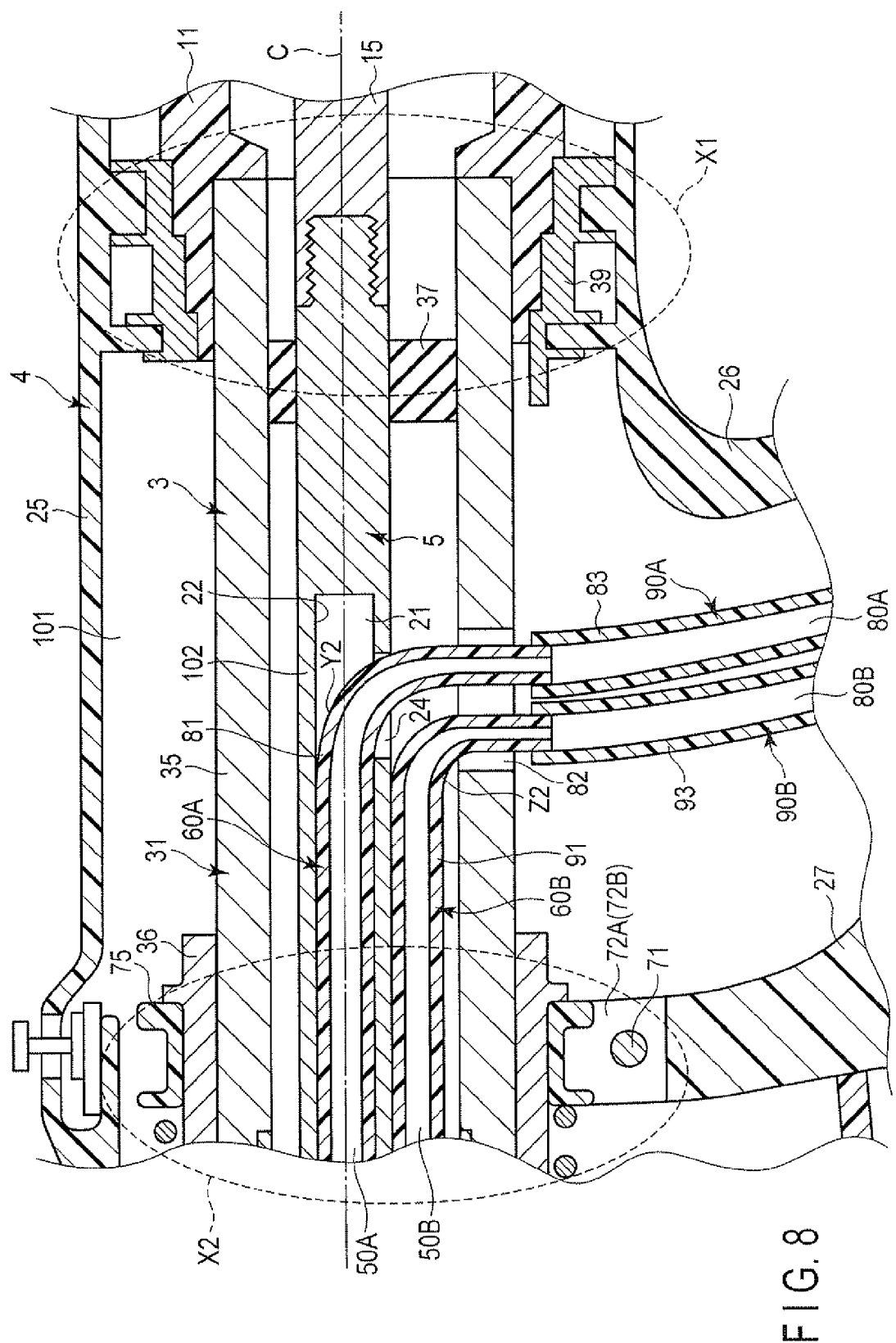
FIG. 8 is a cross-sectional view schematically showing a configuration between a first coupling region and a second coupling region in a cylindrical case according to the first embodiment.

FIG. 8 is a view showing a configuration between the first coupling region X1 and the second coupling region X2 in the cylindrical case 25. As shown in FIG. 8, the opening hole 24 of the probe 5 is placed between the first coupling region X1 and the second coupling region X2. Further, an opening hole 82 extended in the radial directions from an outer peripheral portion of the fixed cylindrical member 35 is provided between the first coupling region X1 and the second coupling region X2. The first suction tube member 81 is bent at the bending position Y2. Further, it is extended to the outer peripheral direction side of the fixed cylindrical member 35 through the opening hole 24 and the opening hole 82. That is, the first suction tube member 81 bent at the bending position Y2 is extended to the outside of the treatment unit (surgery unit) 3 through the outer peripheral portion of the probe 5.

As described above, a first suction path (a first path) 50A that is opened at the opening position Y1 at the distal end portion of the probe 5 is defined by a region of the hole defining surface 22 to the distal direction side of the first suction tube member 81 and the first suction tube member 81. That is, the region of the hole defining surface 22 to the distal direction side of the first suction tube member 81 and the first suction tube member 81 form a first suction path defining portion (a first path defining portion) 60A that defines the first suction path (first aspiration path) 50A. Furthermore, the first suction path defining portion (first aspiration path defining portion) 60A is extended to the bending position Y2 in the probe 5 along the longitudinal axis C. Furthermore, the first suction path defining portion 60A is bent at the bending position Y2, and extended to the outside of the treatment unit 3 through the outer peripheral portion of the probe 5.

Here, the first suction tube member 81 is made of a material having high strength and high heat resistance properties, and its resistance properties with respect to ultrasonic vibration are enhanced. Furthermore, the first suction tube member 81 is made of a material having high elasticity and avoids generation of abnormal noise when coming into contact with the ultrasonically vibrating probe 5. Therefore, as the first suction tube member 81, for example, a polytetrafluoroethylene (PTFE) tube or a polyether ether ketone (PEEK) tube is used. The bending position Y2 of the first suction tube member 81 (the first suction path defining portion 60A) is provided at a node position of the ultrasonic vibration.

As shown in FIG. 4 and FIG. 6, a first liquid supply tube member (a first tube member) 91 is extended between the probe 5 and the sheath portion 31 along the longitudinal axis C. The first liquid supply tube member 91 is extended to a bending position Z2 provided between the first coupling region X1 and the second coupling region X2. That is, the bending position Z2 is provided to the distal direction side of the first coupling region X1, and also provided to the proximal direction side of the second coupling region X2. As shown in FIG. 8, the first liquid supply tube member 91 is bent at the bending position Z2. Further, it is extended to the outer peripheral direction side of the fixed cylindrical member 35 through the opening hole 82. That is, the first liquid supply tube member 81 bent at the bending position Z2 is extended to the outside of the treatment unit 3.

As shown in FIG. 6, in a region to the distal direction side of the first liquid supplying tube member 91, a first liquid supply path (a first path) 50B is defined by the outer peripheral portion of the probe 5 and the inner peripheral portion of the sheath portion 31. The first liquid supply path 50B is opened at the opening position Z1 at the distal end of the sheath portion 31.

As described above, the first liquid supply tube member 91 serves as a first liquid supply path defining portion (a first path defining portion) 60B that defines the first liquid supply path 50B. Furthermore, in the region to the distal direction side of the first liquid supply tube member 91, the outer peripheral portion of the probe 5 and the inner peripheral portion of the sheath portion 31 form the first liquid supply path defining portion 60B that defines the first liquid supply path 50B. The first liquid supply path defining portion 60B is extended to the bending position Z2 between the probe 5 and the sheath portion 31 along the longitudinal axis C. Moreover, the first liquid supply path defining portion 60B is bent at the bending position Z2, and extended from the outer peripheral portion of the probe 5 to the outside of the treatment unit 3.

In addition, as the first liquid supply tube member 91, like the first suction tube member 81, using, e.g., a PTFE tube or a PEEk tube is preferable. Additionally, it is preferable for the bending position Z2 of the first liquid supply tube member 91 (the first liquid supply path defining portion 60B) to be provided at a node position of the ultrasonic vibration.

As shown in FIG. 4 and FIG. 8, in the cylindrical case 25, a second suction tube member (a second tube member) 83 is directly connected to the first suction tube member 81 extended to the outside of the treatment unit 3. The second suction tube member (second aspiration tube member) 83 is extended in the fixed handle 26 along the handle extending direction (the direction of the arrow A in FIG. 4). The second suction tube member 83 is extended to an extending position Y3 provided on the handle extending direction side part of the fixed handle 26.

The second suction tube member 83 has a rigidity lower than that of the first suction tube member 81. Therefore, the second suction tube member 83 is flexible, and it can be readily oriented from the inside of the cylindrical case 25 toward the inside of the fixed handle 26. It is to be noted that, as the second suction tube member 83, a silicone tube or the like can be used.

At the extending position Y3, an external suction tube (an external tube) 85 is connected to the second suction tube 83. The external suction tube (external aspiration tube) 85 is extended from the extending position Y3 to the outside of the handle unit 4. Further, as shown in FIG. 1, the external suction tube 85 is connected to a suction unit (aspiration unit) 87. The suction unit 87 is connected to the control section 10 in the power supply unit 7.

As described above, the second suction tube member 83 and the external suction tube 85 define a second suction path (a second path) 80A communicating with the first suction path 50A outside the treatment unit 3. That is, the second suction tube member 83 and the external suction tube 85 serve as a second suction path defining portion (a second path defining portion) 90A that defines the second suction path (second aspiration path) 80A. The second suction path defining portion (second aspiration path defining portion) 90A is extended in the fixed handle 26 of the handle unit 4 from the outside of the treatment unit 3 along the handle extending direction. Furthermore, the second suction path defining portion 90A is extended to the outside of the handle unit 4 from the extending position Y3 provided on the handle extending direction side part of the fixed handle 26.

As shown in FIG. 4 and FIG. 8, in the cylindrical case 25, a second liquid supply tube member (a second tube member) 93 is directly connected to the first liquid supply tube member 91 extended to the outside of the treatment unit 3. The second liquid supply tube member 93 is extended in the fixed handle 26 along the handle extending direction (the direction of the arrow A in FIG. 4). The second liquid supply tube member 93 is extended to an extending position Z3 provided on the handle extending direction side part of the fixed handle 26.

The second liquid supply tube member 93 has a rigidity lower than that of the first liquid supply tube member 91. Therefore, the second liquid supply tube member 93 is flexible and can be easily oriented from the inside of the cylindrical case 25 toward the inside of the fixed handle 26. It is to be noted that, as the second liquid supply tube member 93, a silicone tube or the like is used.

At the extending position Z3, an external liquid supply tube (an external tube) 95 is connected to the second liquid supply tube member 93. The external liquid supply tube 95 is extended to the outside of the handle unit 4 from the extending position Z3. Furthermore, as shown in FIG. 1, the external liquid supply tube 95 is connected to a liquid supply unit 97. The liquid supply unit 97 is connected to the control section 10 of the power supply unit 7.

As described above, the second liquid supply tube member 93 and the external liquid supply tube 95 define a second liquid supply path (a second path) 80 communicating with the first liquid supply path 50B outside the treatment unit 3. That is, the second liquid supply tube member 93 and the external liquid supply tube 95 form a second liquid supply path defining portion (a second path defining portion) 90B that defines the second liquid supply path 80B. The second liquid supply path defining portion 90B is extended from the outside of the treatment unit 3 in the fixed handle 26 of the handle unit 4 along the handle extending direction. Further, the second liquid supply path defining portion 90B is extended to the outside of the handle unit 4 from the extending position Z3 provided on the handle extending direction side part of the fixed handle 26.

As shown in FIG. 8, the probe 5 includes a cavity forming portion 102 between the first coupling region X1 and the second coupling region X2. When the cavity forming portion 102 is provided in the probe 5, in the cylindrical case 25, a cavity portion 101 is formed between the first coupling region X1 and the second coupling region X2. The cavity forming portion 102 is provided with a dimension larger than a half wavelength of the ultrasonic vibration between the first coupling region X1 and the second coupling region X2 along the longitudinal axis C.

The first suction tube member 81 that is bent at the bending position Y2 is extended to the cavity portion 101 through the outer peripheral portion of the cavity forming portion 101. Further, in the cavity portion 101, the second suction tube member 83 is connected to the first suction tube member 81. As described above, the cavity forming portion 102 has the dimension larger than the half wavelength of the ultrasonic vibration between the first coupling region X1 and the second coupling region X2 along the longitudinal axis C. Therefore, the cavity portion 101 has a size that is sufficient to prevent the second suction tube member 83 from coming into contact with the electrical connection ring 39, the arm portions 72A and 72B of the movable handle 27, and other parts. Since contact with the electrical connection ring 39 and other parts in the cavity portion 101 is avoided, the second suction member 83 does not receive a force from the electrical connection ring 39 or the like. Therefore, crushing or twisting of the second suction tube member 83 in the cavity portion 101 is avoided. Therefore, the second suction tube member 83 can be easily oriented toward the inside of the fixed handle 26 from the cavity portion 101.

Further, the first liquid supply tube member 91 bent at the bending position Z2 is extended to the cavity portion 101 from the outer peripheral portion of the cavity forming portion 102 through the opening hole 82. Furthermore, in the cavity portion 101, the second liquid supply tube member 93 is connected to the first liquid supply tube member 91. As described above, the cavity forming portion 102 has the dimension larger than the half wavelength of the ultrasonic vibration between the first coupling region X1 and the second coupling region X2 along the longitudinal axis C. Therefore, the cavity portion 101 has a size that is sufficient to prevent the second liquid supply tube member 93 to come into contact with the electrical connection ring 39, the arm portions 72A and 72B of the movable handle 27, and other parts. Since the contact with the electrical connection ring 39 and other parts in the cavity portion 101 is avoided, the second liquid supply tube member 93 does not receive a force from the electrical connection ring 39 or the like. Therefore, crushing or twisting of the second liquid supply tube member 93 in the cavity 101 is avoided. Therefore, the second liquid supply tube member 93 can be easily oriented toward the inside of the fixed handle 26 from the cavity portion 101.

Figure 9:
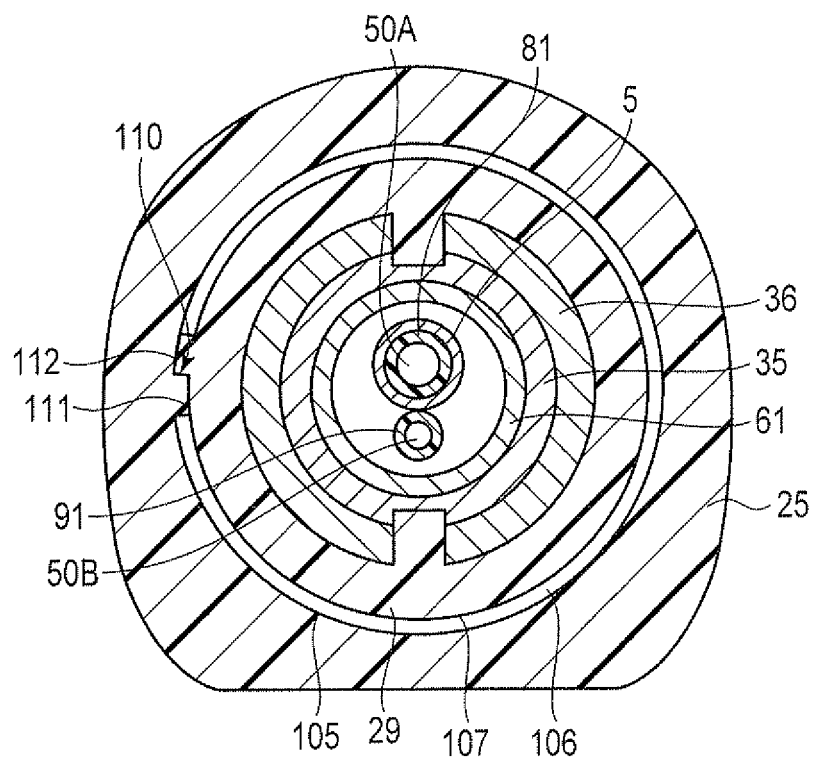
FIG. 9 is a cross-sectional view taken along a line IX-IX in FIG. 4.

FIG. 9 is a cross-sectional view taken along a line IX-IX in FIG. 4. As shown in FIG. 4 and FIG. 9, at the distal end portion of the cylindrical case 25 of the handle unit 4, a protruding portion 105 protruding toward the inner peripheral direction is formed. The protruding portion 105 is extended over all-round circumference of the cylindrical case 25 along the periaxial directions. Further, a groove defining portion 107 that defines a groove-shaped portion 106 that is concave toward the inner peripheral direction is provided on the rotating operation knob 29. The groove defining portion 107 is extended over all-round circumference of the cylindrical case 25 along the periaxial direction. When the protruding portion 105 is inserted into the groove-shaped portion 106, the rotating operation knob 29 is attached to the cylindrical case 25 to be rotatable in the periaxial directions.

The protruding portion 105 of the cylindrical case 25 includes a fixed-side convex portion 111 that protrudes toward the inner peripheral direction beyond other parts of the protruding portion 105. Furthermore, the groove defining portion 107 of the rotating operation knob 29 includes a movable-side convex portion 112 that protrudes toward the outer peripheral direction from a bottom portion. Since the rotating operation knob 29 is attached to the cylindrical case 25 to be rotatable in the periaxial directions, the movable-side convex portion 112 is movable in the periaxial directions with respect to the fixed-side convex portion 111. When the movable-side convex portion 112 comes into contact with the fixed-side convex portion 111, the movement of the movable-side convex portion 112 is regulated by the fixed-side convex portion 111. As described above, the rotation of the rotating operation knob 29 with respect to the cylindrical case 25 is regulated. As a result, when the fixed-side convex portion 111 and the movable-side convex portion 112 are provided between the cylindrical case 25 of the handle unit 4 and the rotating operation knob 29, the rotation range of the rotating operation knob 29 with respect to the cylindrical case 25 in the periaxial directions is regulated to 360° or below. That is, the fixed-side convex portion 111 and the movable-side convex portion 112 form a rotation regulating portion 110 configured to regulate the rotation range of the rotating operation knob 29 with respect to the cylindrical case 25 in the periaxial directions to 360° or below. As a result, the rotation range of the treatment unit 3 (the probe 5, the sheath portion 31, and the jaw 32) with respect to the cylindrical case 25 in the periaxial directions is regulated to 360° or below.

A function of the ultrasonic treatment device 1 according to this embodiment will now be described. In the case of using the ultrasonic treatment device 1 to perform (conduct) a treatment, an operator (surgeon) presses any one of the input buttons 42A to 42C, the first input section 23A, the second input section 23B, and the third input section 23C in accordance with a treatment (surgery). As a result, an electrical signal is transmitted from any one of the switch sections 43A to 43C, the first input section 23A, the second input section 23B, and the third input section 23C to the control section 10 in the power supply unit 7.

When the first input section 23A is pressed, an electric current is supplied from the ultrasonic supply section 8 to the ultrasonic vibrator (ultrasonic oscillator) 12 through the electrical signal lines 13A and 13B, and the ultrasonic vibrator 12 generates the ultrasonic vibration. Further, the ultrasonic vibration is transmitted to the distal end of the probe 5. Moreover, the liquid supply unit 97 is driven, and a liquid such as water (physiological saline) is supplied through the second liquid supply path 80B and the first liquid supply path 50B. At this time, the liquid is supplied to a body tissue (biological tissue) from the opening position Z1 of the first liquid supply path 50B provided at the distal end of the sheath portion 31. Based on the transmission of the ultrasonic vibration and the supply of the liquid to the distal end of the probe 5, cavitation occurs. The cavitation enables selectively shattering (crushing) a body tissue with low elasticity such as a liver tissue. At this time, a body tissue with high elasticity such as a blood vessel is not shattered by the cavitation. Additionally, when the first input section 23A is pressed, the suction unit 87 is driven. Therefore, the body tissue shattered by the cavitation is suctioned (aspirated) from the opening position Y1 in the distal end portion of the probe 5. The body tissue is suctioned and collected by the suction unit 87 through the first suction path 50A and the second suction path 80A. As described above, when the first input section 23A is pressed, the ultrasonic suction is carried out.

Further, when the second input section 23B is pressed, the liquid supply unit 97 alone is driven. As a result, the liquid is supplied from the opening position Z1 through the second liquid supply path 80B and the first liquid supply path 50B. At this time, the ultrasonic vibration is not produced, and the suction unit 87 does not perform suction. Furthermore, when the third input section 23C is pressed, the suction unit 87 alone is driven. As a result, the suction is performed from the opening position Y1 through the first suction path 50A and the second suction path 80A. At this time, the ultrasonic vibration is not generated, and the liquid is not supplied by the liquid supply unit 97.

Moreover, when the input button 42A is pressed, the electric current is supplied from the ultrasonic supply section 8 to the ultrasonic vibrator 12 via the electrical signal lines 13A and 13B, and the ultrasonic vibration is generated. Additionally, the ultrasonic vibration is transmitted to the distal end of the probe 5. At this time, the suction unit 87 and the liquid supply unit 97 are not driven. Friction heat generated by the ultrasonic vibration of the probe 5 enables cutting-and-coagulation with respect to the body tissue such as a blood vessel gripped between the distal end portion of the probe 5 and the jaw 32. As described above, when the input button 42A is pressed, the ultrasonic cutting-and-coagulation is carried out. It is to be noted that, in the ultrasonic cutting-and-coagulation, a high-frequency current may be output from the high-frequency current supply section 9. At this time, the high-frequency current flows through the probe-side current path and the jaw-side current path. Further, the body tissue gripped between the distal end portion of the probe 5 and the jaw 32 is reformed by the high-frequency current, and the coagulation is facilitated.

Further, when the input button 42B is pressed, the high-frequency current flows through the probe-side current path and the jaw-side current path. Furthermore, the distal end portion of the probe 5 and the jaw 32 are used as electrodes, and a bipolar treatment is performed. At this time, the ultrasonic vibration is not generated, and the suction unit 87 is not driven. Moreover, when the input button 42C is pressed, the high-frequency current does not flow through the jaw-side current path, but the high-frequency current flows through the probe-side current path alone. Additionally, the distal end portion of the probe 5 is used as the electrode, and a monopolar treatment is performed. At this time, the ultrasonic vibration is not generated, and the suction unit 87 is not driven. It is to be noted that, in the bipolar treatment (bipolar surgery) and the monopolar treatment (monopolar surgery), the liquid supply unit 97 may be driven. As a result, the bipolar treatment and the monopolar treatment are carried out while dropping the liquid, e.g., physiological saline onto the body tissue.

As described above, when the ultrasonic treatment device 1 is used, both the ultrasonic suction treatment (ultrasonic suction surgery) and the ultrasonic cutting-and-coagulation treatment (ultrasonic cutting-and-coagulation surgery) can be performed without counterchanging or recombining the devices.

Here, at a time of suctioning the body tissue shattered by the cavitation, the body tissue is suctioned and collected by the suction unit 87 through the first suction path 50A and the second suction path 80A. The first suction path defining portion 60A is extended from the opening position Y1 of the distal end portion of the probe 5 to the bending position Y2 in the probe 5 along the longitudinal axis C. Further, the first suction path defining portion 60A is bent at the bending position Y2, and extended to the outside of the treatment unit 3 through the outer peripheral portion of the probe 5. The bending position Y2 is provided to the distal end direction side of the first coupling region X1 of the vibrator unit 2 and the treatment unit 3. Furthermore, outside the treatment unit 3, the first suction path 50A communicates with the second suction path 80A. The second suction path defining portion 90A that defines the second suction path 80A is extended from the outside of the treatment unit 3 in the fixed handle 26 of the handle unit 4 along the handle extending direction. Moreover, the second suction path defining portion 90A is extended from the extending position Y3 provided on the handle extending direction side part of the fixed handle 26 to the outside of the handle unit 4.

Figure 10:
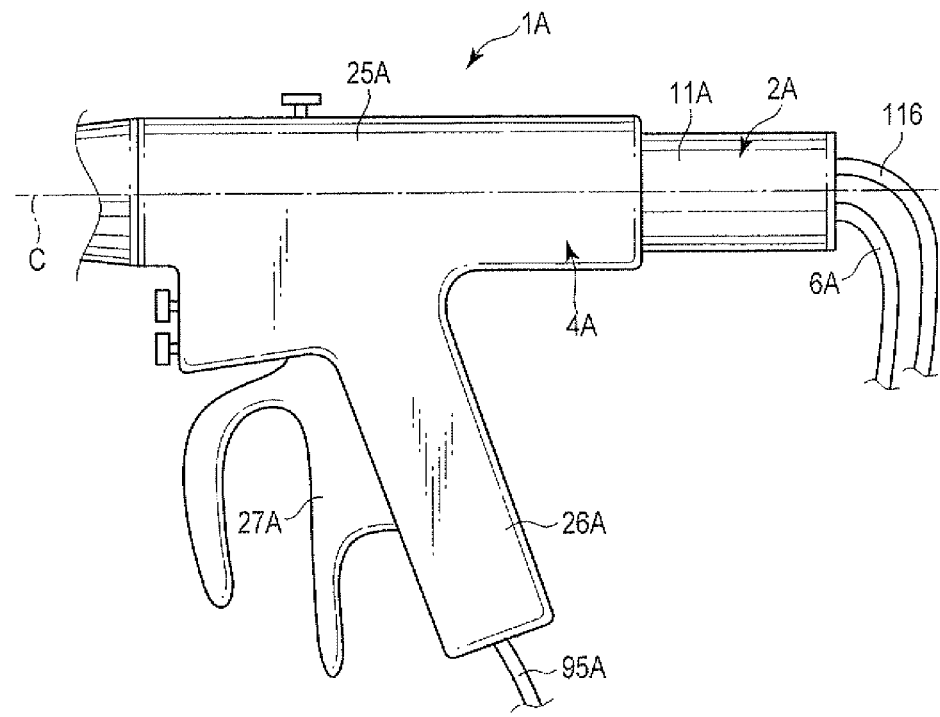
FIG. 10 is a schematic view showing a handle unit and a vibrator unit in an ultrasonic treatment device according to a first comparative example.
Figure 11:
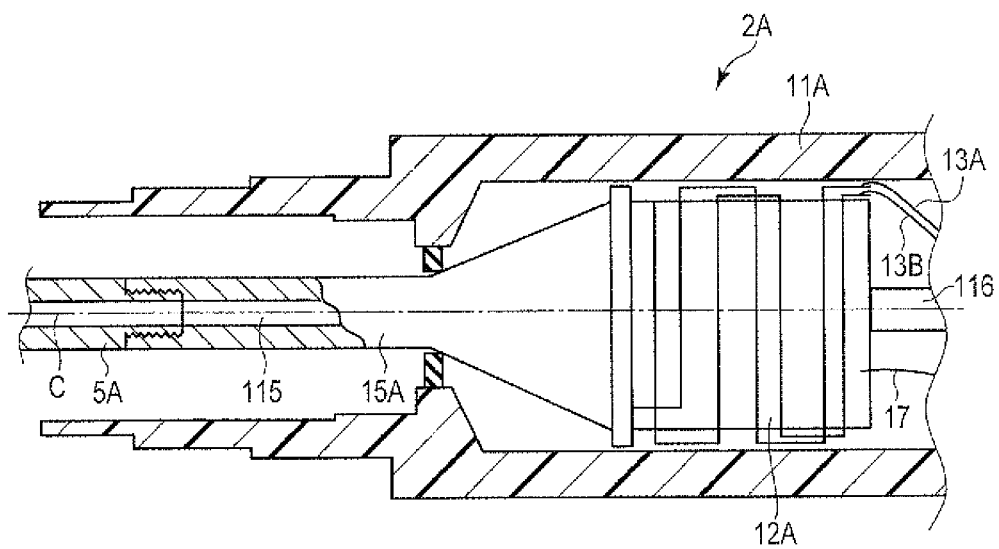
FIG. 11 is a cross-sectional view schematically showing an internal configuration of a vibrator unit according to the first comparative example.

Here, as a first comparative example, as shown in FIG. 10 and FIG. 11, an ultrasonic treatment device 1A will now be considered. As shown in FIG. 10, in the ultrasonic treatment device 1A, a suction path 115 is extended from an inside of a probe 3A via an inside of a horn 15A and an inside of an ultrasonic vibrator 12A along the longitudinal axis C. The suction path 115 is connected to a suction tube 116 at a proximal end portion of the ultrasonic vibrator 12A. Moreover, as shown in FIG. 11, the suction tube 116 is extended to the outside of a vibrator case 11A of a vibrator unit 2A.

In terms of materials and costs, generally, the ultrasonic vibrator (12, 12A) is not disposed, and it is reused. Therefore, in the ultrasonic treatment device (1, 1A), a treatment unit (3, 3A) and a handle unit (4, 4A) are disposed after use, and the vibrator unit (2, 2A) is reused. In the ultrasonic treatment device 1A, since the suction path 115 is provided in the ultrasonic vibrator 12A, sterilization and cleaning are required after use. Further, the suction tube 116 connected to the vibrator unit 2A is disposed after use. Therefore, after use of the ultrasonic treatment device 1A, the vibrator unit 2A must be removed from the handle unit 4A, and the suction tube 116 must be removed from the vibrator unit 2A. In preparation of assembling the ultrasonic treatment device 1A, the vibrator unit 2A must be coupled with the handle unit 4A, and the suction tube 116 must be connected to the vibrator unit 2A.

On the other hand, in the ultrasonic treatment device 1 according to this embodiment, the first suction path defining portion 60A and the second suction path defining portion 90A are not provided in the vibration unit 2. Therefore, the vibrator unit 2 does not have to be sterilized and cleaned after use. Furthermore, in the ultrasonic treatment device 1, the first suction tube member 81, the second suction tube member 83, and the external suction tube 85 are disposed without being removed from the handle unit 4 and the treatment unit 3. That is, in the ultrasonic treatment device 1, just removing the vibrator unit 2 from the cylindrical case 25 (the handle unit 4) and the treatment unit 3 enables integrally disposing (discarding) the first suction tube member 81, the second suction tube member 83, and the external suction tube 85 with the handle unit 4 and the treatment unit 3.

Moreover, at a time of assembling the ultrasonic treatment device 1, the assembly preparation can be easily carried out. For example, the first suction tube member 81 is formed integrally with the treatment unit 3, and the second suction tube member 83 and the external suction tube 85 are formed integrally with the handle unit 4. Additionally, in the cylindrical case 25, the second suction tube member 83 is connected to the first suction tube member 81, and then the treatment unit 3 is coupled with the cylindrical case 25 from the distal direction side. Further, the vibrator unit 2 is coupled with the cylindrical case 25 from the proximal direction side, and the treatment unit 3 is coupled with the vibrator unit 2 in the first coupling region X1. As a result, the ultrasonic treatment device 1 is assembled without connecting the second suction tube member 83 and the external suction tube 85 to the vibrator unit 2. As described above, in the ultrasonic treatment device 1 according to this embodiment, the processing after use, the assembly preparation, and other tasks can be easily carried out.

Furthermore, in general, one end of the cable (6, 6A), in which the electrical signal lines 13A and 13B and the like through which an electric current is supplied to the ultrasonic vibrator (12, 12A) are extended, is connected to the vibrator unit (2, 2A). Therefore, in the ultrasonic treatment device 1 according to the first comparative example in which the suction tube 116 is connected to the vibrator unit 2A, a weight on the proximal direction side part of the handle unit 4A is larger. In general, an operator performs a treatment (surgery) while gripping the fixed handle 26 and the movable handle 27 in the handle unit (4, 4A). Therefore, since the weight of a part to the proximal direction side of the handle unit 4A becomes larger, the center of gravity is located to the proximal direction side of a position where the operator grips, and the balance of the center of gravity at the time of a treatment becomes poor.

On the other hand, in this embodiment, the first suction path defining portion 60A is bent at the bending position Y2 provided to the distal direction side of the first coupling region X1, and is extended to the outside of the treatment unit 3 through the outer peripheral portion of the probe 5. Further, the second suction path defining portion 90A connected to the first suction path defining portion 60A outside the treatment unit 3 is extended in the fixed handle 26 of the handle unit 4 along the handle extending direction. Furthermore, the second suction path defining portion 90A is extended to the outside of the handle unit 4 from the extending position Y3 provided on the handle extending direction side part of the fixed handle 26. Likewise, the first liquid supply path defining portion 60B is bent at the bending position Z2 provided to the distal direction side of the first coupling region X1, and extended to the outside of the treatment unit 3 from the outer peripheral portion of the probe 5. Furthermore, the second liquid supply path defining portion 90B connected to the first liquid supply path defining portion 60B outside the treatment unit 3 is extended in the fixed handle 26 of the handle unit 4 along the handle extending direction. Moreover, the second liquid supply path defining portion 90B is extended to the outside of the handle unit 4 from the extending position Z3 provided on the handle extending direction side part of the fixed handle 26.

As described above, in this embodiment, the second suction path defining portion 90A and the second liquid supply path defining portion 90B, passing through the inside of the fixed handle 26, are extended to the outside of the handle unit 4 from the extending position (Y3, Z3) located on the handle extending direction side part of the fixed handle 26. Therefore, the weight of the part to the proximal direction side of the handle unit 4 is not increased, and the center of gravity of the ultrasonic treatment device 1 is placed on the handle unit 4. Therefore, in the case of performing a treatment while gripping the fixed handle 26 and the movable handle 27, a position where an operator grips coincides with the position of the center of gravity in directions parallel to the longitudinal axis C. As a result, the treatment is performed with an excellent balance of the center of gravity, and the distal end portion of the probe 5 and the jaw 32 can be readily positioned at the time of a treatment. Therefore, the operability during the treatment can be improved.

Moreover, in the case of performing the ultrasonic cutting-and-coagulation, when the rotating operation knob 29 is rotated with respect to the cylindrical case 25, the probe 5 and the jaw 32 rotate in one of the periaxial directions with respect to the cylindrical case 25. At this time, the fixed-side convex portion 111 and the movable-side convex portion 112 regulate the rotation range of the rotating operation knob 29 (the treatment unit 3) in the periaxial directions with respect to the cylindrical case 25 to 360° or below.

The cavity forming portion 102 of the probe 5 is provided with a dimension larger than the half wavelength of the ultrasonic vibration between the first coupling region X1 and the second coupling region X2 along the longitudinal axis C. Therefore, in the cylindrical case 25, the cavity portion 101 is formed between the first coupling region X1 and the second coupling region X2. The first suction tube member 81 bent at the bending position Y2 is extended to the cavity portion 101 through the outer peripheral portion of the cavity forming portion 102. Additionally, in the cavity portion 101, the second suction tube member 83 is connected to the first suction tube member 81. Further, the first liquid supply tube member 91 bent at the bending position Z2 is extended to the cavity portion 101 from the outer periphery of the cavity forming portion 102 through the opening hole 82. Furthermore, in the cavity portion 101, the second liquid supply tube member 93 is connected to the first liquid supply tube member 91.

Figure 12:
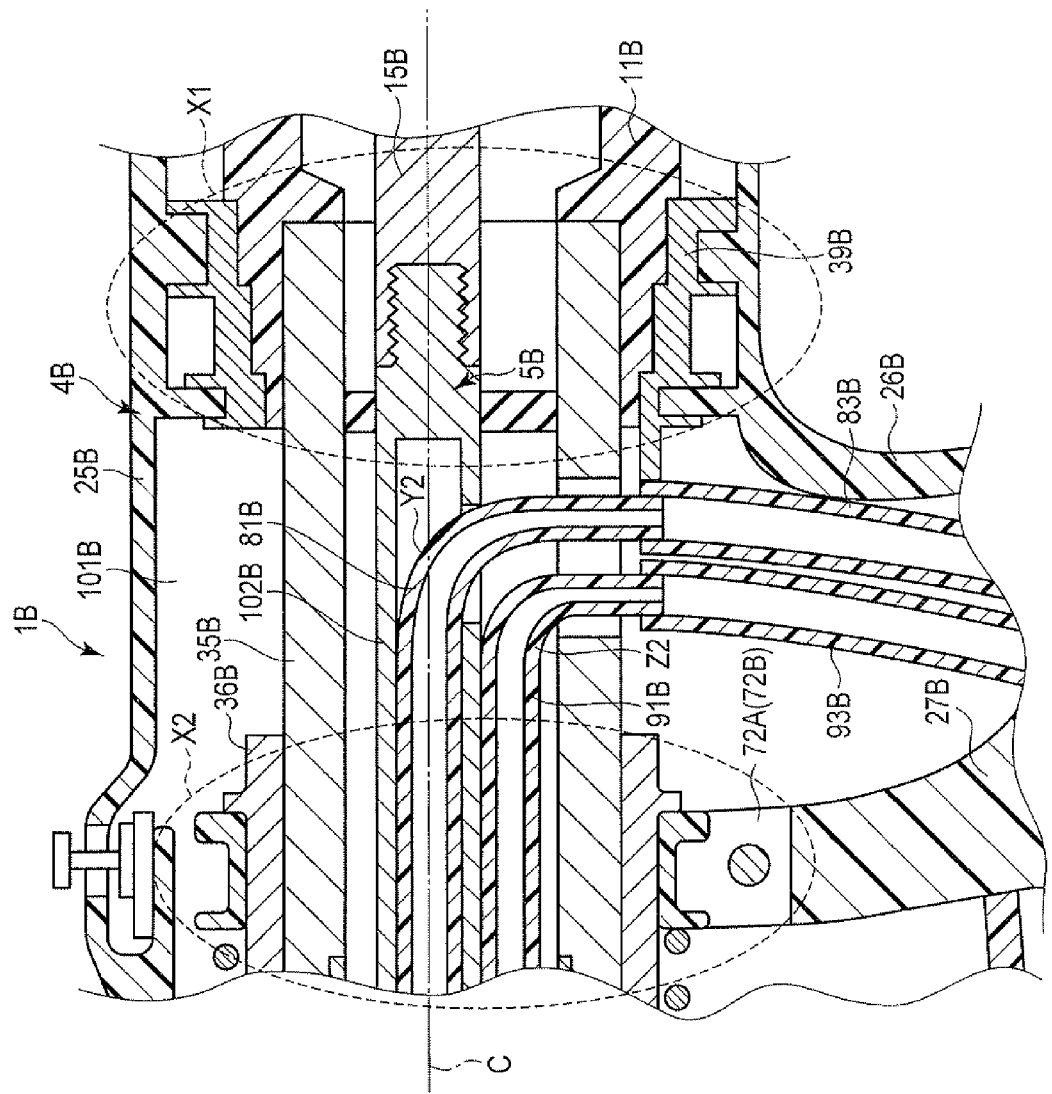
FIG. 12 is a cross-sectional view schematically showing a configuration between a first coupling region and a second coupling region in a cylindrical case in an ultrasonic treatment device according to a second comparative example.

Here, as a second comparative example, as shown in FIG. 12, an ultrasonic treatment device 1B will now be considered. As shown in FIG. 12, in the ultrasonic treatment device 1B, a dimension of a cavity forming portion 102B in a probe 5B between a first coupling region X1 and a second coupling region X2 along the longitudinal axis C is smaller than the half wavelength of the ultrasonic vibration. Therefore, a cavity portion 101B in the cylindrical case 52B is narrower than the cavity portion 101 in the first embodiment. It is to be noted that, in this reference example, a bending position Y2 of a first suction tube member 81B is provided between the first coupling region X1 and the second coupling region X2. Furthermore, in the cavity portion 101B, the second suction tube member 83B is connected to the first suction tube member 81B. Likewise, a bending position Z2 of a first liquid supply tube member 91B is provided between the first coupling region X1 and the second coupling region X2. Moreover, in the cavity portion 101B, a second liquid supply tube member 93B is connected to a first liquid supply tube member 91B.

In this comparative example, since the cavity portion 101B is narrow, the second suction tube member 83B and the second liquid supply tube member 93B are apt to come into contact with an electrical connection ring 39B, arm portions 72A and 72B of a movable handle 27B, and other parts in a cylindrical case 25B. That is, the cavity portion 101B is not of a size sufficient to prevent the second suction tube member 83B and the second liquid supply tube member 93B from coming into contact with the electrical connection ring 39, arm portions 72A and 72B of a movable handle 27B, and other parts. When the second suction tube member 83B and the second liquid supply tube member 93B come into contact with the electrical connection ring 39B and other parts, they receive a force from the electrical connection ring 39B and other parts. Upon receiving the force from the electrical connection ring 39B and other parts, the second suction tube member 83B and the second liquid supply tube member 93B are crushed and twisted in the cavity portion 101B. Therefore, it is difficult to orient the second suction tube member 83B and the second liquid supply tube member 93B from the cavity portion 101B toward the inside of the fixed handle 26B. Further, when the second suction tube member 83B and the second liquid supply tube member 93B are crushed and twisted and the treatment unit 3B thereby rotates in the periaxial directions, the second suction tube member 83B and the second liquid supply tube member 93B are apt to wind around the outer peripheral portion of the sheath portion 31B.

On the other hand, in this embodiment, the cavity forming portion 102 of the probe 5 is provided with a dimension larger than the half wavelength of the ultrasonic vibration between the first coupling region X1 and the second coupling region X2 along the longitudinal axis C. Furthermore, the cavity forming portion 102 forms the cavity portion 101. Therefore, the cavity portion 101 has a size that is sufficient to prevent the second suction tube member 83 and the second liquid supply tube member 93 from coming into contact with the electrical connection ring 39, the arm portions 72A and 72B of the movable handle 27, and other parts. Since contact with the electrical connection ring 39 and other parts in the cavity portion 101 is avoided, the second suction tube member 83 and the second liquid supply tube member 93 do not receive a force from the electrical connection ring 39 and other parts. Therefore, crushing and twisting of the second suction tube member 83 and the second liquid supply tube member 93 in the cavity portion 101 are avoided. Accordingly, the second suction tube member 83 and the second liquid supply tube member 93 can be readily oriented toward the inside of the fixed handle 26 from the cavity portion 101.

Further, since the second suction tube member 83 and the second liquid supply tube member 93 are not crushed and twisted, when the treatment unit 3 rotates in the periaxial directions, the second suction tube member 83 and the second liquid supply tube member 93 are apt to wind around the outer peripheral portion of the sheath portion 31. In a state that the second suction tube member 83 and the second liquid supply tube member 93 are not in contact with the electrical connection ring 39 and other parts, when the rotation range of the treatment unit 3 is set to 360° or below, the second suction tube member 83 and the second liquid supply tube member 93 can be prevented from winding around the outer peripheral portion of the sheath portion 31. In this embodiment, the fixed-side convex portion 111 and the movable-side convex portion 112 are configured to regulate the rotation range of the rotating operation knob 29 in the periaxial directions with respect to the cylindrical case 25 to 360° or below. Therefore, the rotation range of the treatment unit 3 is also regulated to 360° or below. Therefore, when the treatment unit 3 rotates in the periaxial directions, the second suction tube member 83 and the second liquid supply tube member 93 can be effectively prevented from winding around the outer peripheral portion of the sheath portion 31.

As described above, in this embodiment, in the probe 5, the cavity forming portion 102 having a dimension larger than the half wavelength of the ultrasonic vibration is provided between the first coupling region X1 and the second coupling region X2 along the longitudinal axis C. Further, the fixed-side convex portion 111 is provided to the cylindrical case 25, and the movable-side convex portion 112 is provided to the rotating operation knob 29. When such a configuration is adopted, the second suction tube member 83 and the second liquid supply tube member 93 can be prevented from winding around the outer peripheral portion of the sheath portion 31. That is, the second suction tube member 83 and the second liquid supply tube member 93 are prevented from winding around the outer peripheral portion of the sheath portion 31 without providing different members other than members required in a treatment using the ultrasonic treatment device 1.

Furthermore, the second suction tube member 83 has a rigidity lower than that of the first suction tube member 81, and the second liquid supply tube member 93 has a rigidity lower than that of the first liquid supply tube member 91. Therefore, in the cavity portion 101, the second suction tube member 83 and the second liquid supply tube member 93 can easily bend. Therefore, the second suction tube member 83 and the second liquid supply tube member 93 can be easily oriented from the inside of the cylindrical case 25 toward the inside of the fixed handle 26.

Moreover, the bending position Y2 of the first suction tube member 81 (the first suction path defining portion 60A) is provided at a node position of the ultrasonic vibration. Likewise, the bending position Z2 of the first liquid supply tube member 91 (the first liquid supply path defining portion 60B) is provided at the node position of the ultrasonic vibration. At the node position of the ultrasonic vibration, a displacement due to the ultrasonic vibration is zero. Therefore, the first suction tube member 81 is hardly affected by the ultrasonic vibration at the bending position Y2, and the first suction tube member 81 is effectively prevented from being damaged. Likewise, the first liquid supply tube member 91 is hardly affected by the ultrasonic vibration at the bending position Z2, and the first liquid supply tube member 91 is effectively prevented from being damaged.

Therefore, the ultrasonic treatment device 1 having the above-described configuration provides the following effects. That is, the ultrasonic treatment device 1 can provide both the ultrasonic suction treatment and the ultrasonic cutting-and-coagulation treatment without, e.g., counterchanging or recombining the devices.

Additionally, in the ultrasonic treatment device 1, the first suction path defining portion 60A and the second suction path defining portion 90A are not provided in the vibrator unit 2. Therefore, the vibrator unit 2 does not have to be sterilized or cleaned after use. Further, in the ultrasonic treatment device 1, the first suction tube member 81, the second suction tube member 83, and the external suction tube 85 are disposed without being removed from the handle unit 4 and the treatment unit 3. That is, in the ultrasonic treatment device 1, just removing the vibrator unit 2 from the cylindrical case 25 (the handle unit 4) and the treatment unit 3 enables integrally disposing the first suction tube member 81, the second suction tube member 83, and the external suction tube 85 with the handle unit 4 and the treatment unit 3. Furthermore, the ultrasonic treatment device 1 can be assembled without connecting the second suction tube member 83 and the external suction tube 85 to the vibrator unit 2. As described above, in accordance with the ultrasonic treatment device 1 according to this embodiment, the processing after use, the assembly preparation, and other tasks can be readily carried out.

Moreover, in the ultrasonic treatment device 1, the second suction path defining portion 90A and the second liquid supply path defining portion 90B pass through the inside of the fixed handle 26, and are extended to the outside of the handle unit 4 from the extending position (Y3, Z3) of the fixed handle 26 located on the handle extending direction side part. Therefore, the weight on a part to the proximal direction side of the handle unit 4 is not increased, and the center of gravity of the ultrasonic treatment device 1 is within the handle unit 4. Therefore, at a time of performing a treatment while gripping the fixed handle 26 and the movable handle 27, a position where an operator (surgeon) grips coincides with the position of the center of gravity in the directions parallel to the longitudinal axis C. As a result, the treatment can be performed with excellent balance of the center of gravity, and the distal end portion of the probe 5 and the jaw 32 can be readily positioned at the time of the treatment. Therefore, the operability during the treatment can be improved.

Additionally, in the ultrasonic treatment device 1, the probe 5 includes a cavity forming portion 102 having a dimension larger than the half wavelength of the ultrasonic vibration between the first coupling region X1 and the second coupling region X2 along the longitudinal axis C. Further, the cavity forming portion 102 forms the cavity portion 101. Therefore, the cavity portion 101 has a size that is sufficient to prevent the second suction tube member 83 and the second liquid supply tube member 93 from coming into contact with the electrical connection ring 39, the arm portions 72A and 72B of the movable handle 27, and other parts. Since contact with the electrical connection ring 39 and other parts is avoided in the cavity portion 101, the second suction tube member 83 and the second liquid supply tube member 93 do not receive force from the electrical connection ring 39 and other parts. Therefore, crushing or twisting of the second suction tube member 83 and the second liquid supply tube member 93 in the cavity portion 101 can be prevented. Accordingly, the second suction tube member 83 and the second liquid supply tube member 93 can be easily orientated from the cavity portion 101 toward the inside of the fixed handle 26.

Further, in the ultrasonic treatment device 1, since the second suction tube member 83 and the second liquid supply tube member 93 are not crushed or twisted, when the treatment unit 3 rotates in the periaxial directions, it is difficult for the second suction tube member 83 and the second liquid supply tube member 93 to wind around the outer peripheral portion of the sheath portion 31. In a state that the second suction tube member 83 and the second liquid supply tube member 93 are not in contact with the electrical connection ring 39 and others, setting the rotation range of the treatment unit 3 to 360° or below enables preventing the second suction tube member 83 and the second liquid supply tube member 93 from winding around the outer peripheral portion of the sheath portion 31. Here, the fixed-side convex portion 111 and the movable-side convex portion 112 are configured to regulate the rotation range of the rotating operation knob 29 in the periaxial directions with respect to the cylindrical case 25 to 360° or below. Therefore, the rotation range of the treatment unit 3 is also regulated to 360° or below. Therefore, when the treatment unit 3 rotates in the periaxial directions, the second suction tube member 83 and the second liquid supply tube member 93 can be effectively prevented from winding around the outer peripheral portion of the sheath portion 31.

Furthermore, in the ultrasonic treatment device 1, it is possible to prevent the second suction tube member 83 and the second liquid supply tube member 93 from winding around the outer peripheral portion of the sheath portion 31 without providing different members other than members required in a treatment using the ultrasonic treatment device 1.

Moreover, in the ultrasonic treatment device 1, the second suction tube member 83 has a rigidity lower than that of the first suction tube member 81, and the second liquid supply tube member 93 has a rigidity lower than that of the first liquid supply tube member 91. Therefore, in the cavity portion 101, the second suction tube member 83 and the second liquid supply tube member 93 can easily bend. Therefore, the second suction tube member 83 and the second liquid supply tube member 93 can be further easily oriented from the inside of the cylindrical case 25 toward the inside of the fixed handle 26.

Further, in the ultrasonic treatment device 1, the bending position Y2 of the first suction tube member 81 (the first suction path defining portion 60A) is provided at a node position of the ultrasonic vibration. Likewise, the bending position Z2 of the first liquid supply tube member 91 (the first liquid supply path defining portion 60B) is provided at a node position of the ultrasonic vibration. At the node position of the ultrasonic vibration, a displacement caused due to the ultrasonic vibration is zero. Therefore, the first suction tube member 81 is hardly affected by the ultrasonic vibration at the bending position Y2, and the first suction tube member 81 can be effectively prevented from being damaged. Likewise, the first liquid supply tube member 91 is hardly affected by the ultrasonic vibration at the bending position Z2, and the first liquid supply tube member 91 can be effectively prevented from being damaged.

Modification of First Embodiment

It is to be noted that although the movable handle 27 is placed to the distal direction side of the fixed handle 26, the present invention is not restricted thereto. For example, as a first modification, as shown in FIG. 13, the movable handle 27 may be placed to the proximal direction side of the fixed handle 26. In this modification, like the first embodiment, the movable handle 27 is openable or closable with respect to the fixed handle 26 substantially in parallel with respect to the longitudinal axis C. Moreover, in accordance with the opening/closing operation of the movable handle 27, the movable portion 70 (see FIG. 4 and FIG. 6) of the sheath portion 31 moves with respect to the handle unit 4 and the probe 5 along the longitudinal axis C. When the movable portion 70 moves along the longitudinal axis C, the jaw 32 is opened or closed with respect to the distal end portion of the probe 5.

Figure 14:
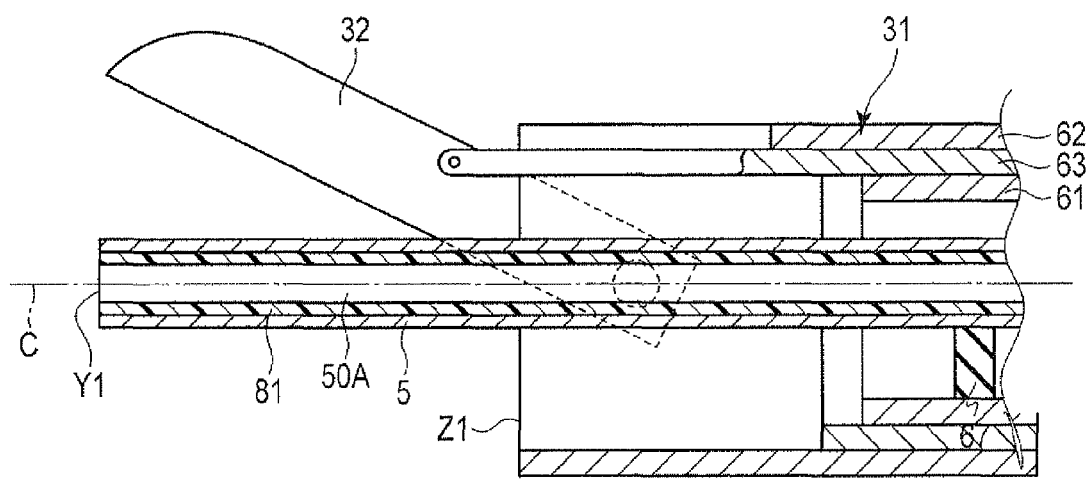
FIG. 14 is a cross-sectional view schematically showing a state that a probe is inserted through a sheath portion of an ultrasonic treatment device according to a second modification of the first embodiment.

Additionally, in the first embodiment, although the distal end of the first suction tube member 81 is placed between the bending position Y2 and the opening position Y1 of the first suction path defining portion 60A, the present invention is not restricted thereto. For example, as a second modification, as shown in FIG. 14, the first suction tube member 81 may be extended to the opening position Y1 at the distal end of the first suction path defining portion 60A. In this case, the distal end of the first suction tube member 81 coincides with the opening position Y1 of the first suction path defining portion 60A. As described above, based on the second modification, the first suction tube member 81 may be extended to the bending position Y2 along the longitudinal axis C in the hole-shaped portion 21 of the probe 5. Further, the first suction tube member 81 can be extended from the bending position Y2 to the outside of the treatment unit 3 through the outer peripheral portion of the probe 5.

Furthermore, in the first liquid supply tube member 91, it can be described the same matter as the first suction tube member 81. That is, the first liquid supply tube member 91 may be extended to the opening position Z1 at the distal end of the first liquid supply path defining portion 60B.

Second Embodiment

A second embodiment according to the present invention will now be described with reference to FIG. 15 to FIG. 17. The second embodiment can be obtained by modifying the configuration of the first embodiment as follows. It is to be noted that like reference numerals denote parts equal to those in the first embodiment, and a description thereof will be omitted.

Figure 15:
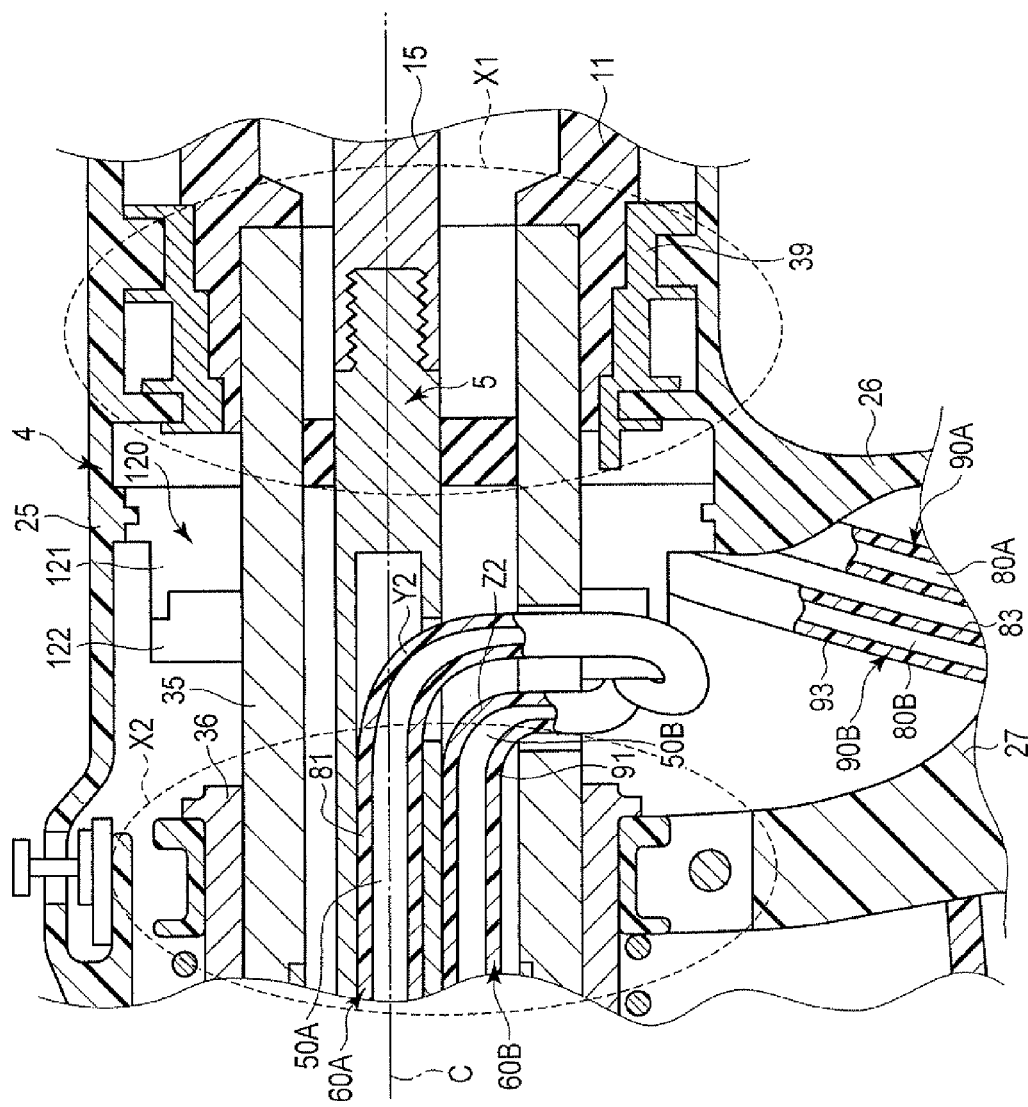
FIG. 15 is a cross-sectional view schematically showing a configuration between a first coupling region and a second coupling region in a cylindrical case of an ultrasonic treatment device according to a second embodiment of the present invention.

FIG. 15 is a view showing a configuration between a first coupling region X1 and a second coupling region X2 in a cylindrical case 25 according to this embodiment. As shown in FIG. 15, a dimension of a probe 5 according to this embodiment between the first coupling region X1 and the second coupling region X2 along a longitudinal axis C is smaller than a half wavelength of an ultrasonic wave. Moreover, in this embodiment, in the cylindrical case 25, a fixed-side member 121 and a movable-side member 122 are provided. Therefore, in the cylindrical case 25, a cavity portion 101 is not formed.

The movable-side member 122 is coupled with the fixed-side member 121 to be rotatable in periaxial directions. The fixed-side member 121 is provided in a fixed state with respect to the cylindrical case 25. The movable-side member 122 is provided in a fixed state with respect to an outer peripheral portion of a fixed cylindrical member 35 of a sheath portion 31. Therefore, the movable-side member 122 rotatable with respect to the fixed-side member 121 and the cylindrical case 25 in the periaxial directions integrally with the sheath portion 31 (a treatment unit 3).

The fixed-side member 121 and the movable-side member 122 are placed between the first coupling region X1 and the second coupling region X2. In this embodiment, likewise, a first suction tube member 81 is bent at a bending position Y2 between the first coupling region X1 and the second coupling region X2, and extended to an outside of the treatment unit 3. Likewise, a first liquid supply tube member 91 is bent at a bending position Z2 between the first coupling region X1 and the second coupling region X2, and extended to the outside of the treatment unit 3. The first suction tube member 81 and the first liquid supply tube member 91 are connected to the movable-side member 122 outside the treatment unit 3. Further, a second suction tube member 83 and a second liquid supply tube member 93 are connected to the fixed-side member 121 outside the treatment unit 3. That is, the fixed-side member 121 and the movable-side member 122 connect the first suction tube member 81 to the second suction tube member 83. Furthermore, the fixed-side member 121 and the movable-side member 122 connect the first liquid supply member 91 to the second liquid supply tube member 93.

Figure 16:
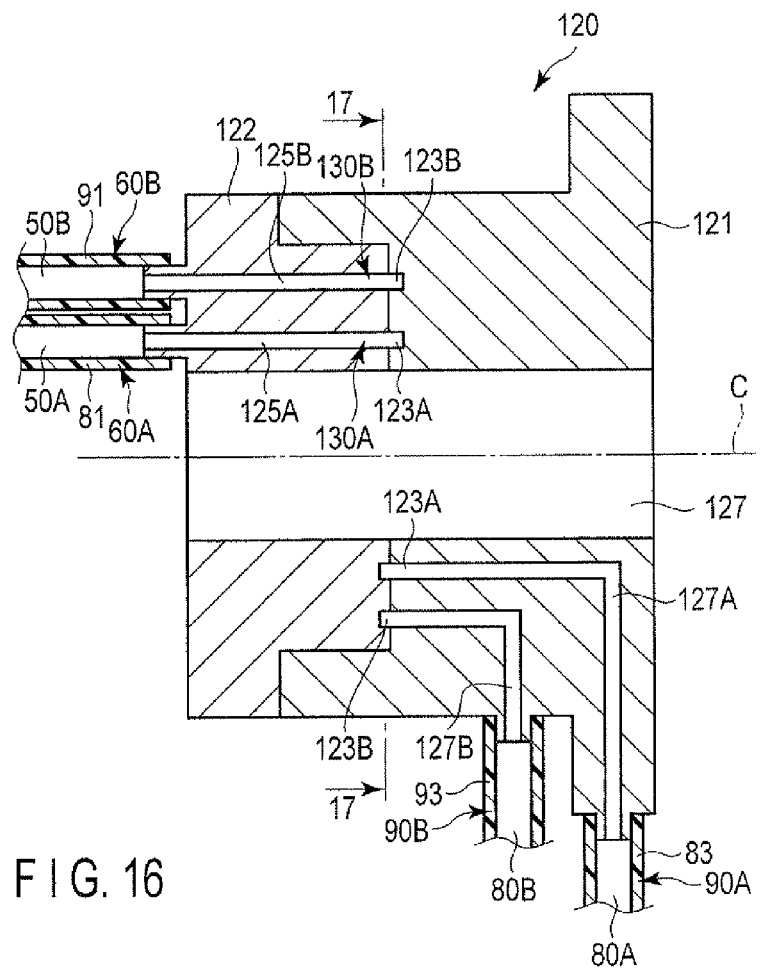
FIG. 16 is a cross-sectional view schematically showing a state that a fixed-side member is coupled with a movable-side member according to the second embodiment.
Figure 17:
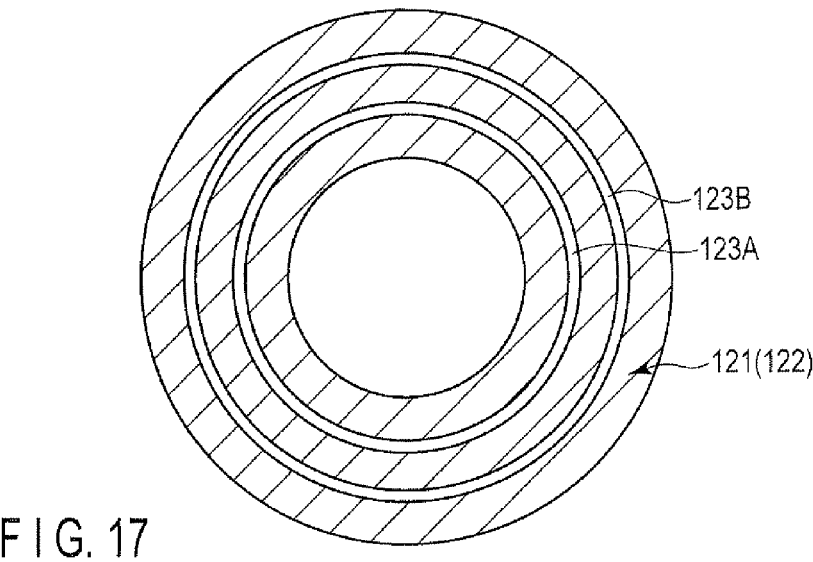
FIG. 17 is a cross-sectional view taken along a line 17-17 in FIG. 16.

FIG. 16 is a view showing a state in which the fixed-side member 121 is coupled with the movable-side member 122. FIG. 17 is a cross-sectional view taken along a line 17-17 in FIG. 16. As shown in FIG. 16 and FIG. 17, in the state that the fixed-side member 121 is coupled with the movable-side member 122, a first suction intermediate cavity (first aspiration intermediate cavity) 123A is provided between the fixed-side member 121 and the movable-side member 122. The first suction intermediate cavity 123A is provided to form a circle in periaxial directions. Additionally, in the state that fixed-side member 121 is coupled with the movable-side member 122, a first liquid supply intermediate cavity 123B is provided between the fixed-side member 121 and the movable-side member 122. The first liquid supply intermediate cavity 123B is placed to the outer peripheral direction side of the first suction intermediate cavity 123A, and it is provided to form a circle in the periaxial directions. As described above, each of the first suction intermediate cavity 123A and the first liquid supply intermediate cavity 123B is provided to form the circle in the periaxial directions between the fixed-side member 121 and the movable-side member 122 irrespective of a state of rotation of the movable-side member 122 with respect to the fixed-side member 121.

A second suction intermediate cavity (second aspiration intermediate cavity) 125A and a second liquid supply intermediate cavity 125B are provided to the movable-side member 122 along the longitudinal axis C. When the first suction tube member 81 is connected to the movable-side member 122, a first suction path 50A communicates with the second suction intermediate cavity 125A. The second suction intermediate cavity 125A communicates with the first suction intermediate cavity 123A irrespective of the state of rotation of the movable-side member 122 with respect to the fixed-side member 121. Further, when the first liquid supply tube member 91 is connected to the movable-side member 122, a first liquid supply path 50B communicates with the second liquid supply intermediate cavity 125B. The second liquid intermediate cavity 125B communicates with the first liquid supply intermediate cavity 123B irrespective of the state of rotation of the movable-side member 122 with respect to the fixed-side member 121.

A third suction intermediate cavity (third aspiration intermediate cavity) 127A and a third liquid supply intermediate cavity 127B each having an L-like shape are provided in the fixed-side member 121. When the second suction tube member 83 is connected to the fixed-side member 121, a second suction path 80A communicates with the third suction intermediate cavity 127A. The third suction intermediate cavity 127A communicates with the first suction intermediate cavity 123A irrespective of the state of rotation of the movable-side member 122 with respect to the fixed-side member 121. Further, when the second liquid supply tube member 93 is connected to the fixed-side member 121, a second liquid supply path 80B communicates with the third liquid supply intermediate cavity 127B. The third liquid supply intermediate cavity 127B communicates with the first liquid supply intermediate cavity 123B irrespective of the state of rotation of the movable-side member 122 with respect to the fixed-side member 121.

As described above, the first suction intermediate cavity 123A, the second suction intermediate cavity 125A, and the third suction intermediate cavity 127A form a suction intermediate path (an intermediate path) 130A that intermediates between the first suction path 50A and the second suction path 80A. The fixed-side member 121 and the movable-side member 122 cooperatively define the suction intermediate path 130A so that the first suction path 50A communicates with the second suction path 80A irrespective of the state of rotation of the movable-side member 122 with respect to the fixed-side member 121. Furthermore, the first liquid supply intermediate cavity 123B, the second liquid supply intermediate cavity 125B, and the third liquid supply intermediate cavity 127B form a liquid supply intermediate path (an intermediate path) 130B that intermediates between the first liquid supply path 50B and the second liquid supply path 80B. The fixed-side member 121 and the movable-side member 122 cooperatively define the liquid supply intermediate path 130B so that the first liquid supply path 50B communicates with the second liquid supply path 80B irrespective of the state of rotation of the movable-side member 122 with respect to the fixed-side member 121. Moreover, the fixed-side member 121 and the movable-side member 122 form an intermediate path defining portion 120 that defines the suction intermediate path 130A and the liquid supply intermediate path 130B.

In this embodiment, the second suction tube member 83 and the second liquid supply tube member 93 are connected to the fixed-side member 121. The fixed-side member 121 is provided in the fixed state with respect to the cylindrical case 25 of the handle unit 4. Therefore, when the treatment unit 3 and the movable-side member 122 rotate in the periaxial directions integrally with a rotating operation knob 29, the fixed-side member 121, the second suction tube member 83, and the second liquid supply tube member 93 do not rotate. Therefore, when the treatment unit 3 rotates in the periaxial directions, the second suction tube member 83 and the second liquid supply tube member 93 are effectively prevented from winding around the outer peripheral portion of the sheath portion 31.

Further, since the fixed-side member 121 to which the second suction tube member 83 and the second liquid supply tube member 93 are connected is not rotated, as differs from the first embodiment, the rotation range of the treatment unit 3 does not have to be restricted to 360° or below. Therefore, a rotation regulating portion 110 configured to regulate the rotation range of the rotating operation knob 29 with respect to the cylindrical case 25 in the periaxial directions to 360° or below does not have to be provided between the cylindrical case 25 and the rotating operation knob 29. Therefore, a fixed-side convex portion 111 and a movable-side convex portion 112 do not have to be provided between the cylindrical case 25 and the rotating operation knob 29, and a configuration between the cylindrical case 25 and the rotating operation knob 29 is simplified.

Therefore, in the ultrasonic treatment device 1 having the above-described configuration, the following effects are exercised in addition to the same effects as those of the first embodiment. That is, in the ultrasonic treatment device 1, the second suction tube member 83 and the second liquid supply member 93 are connected to the fixed-side member 121. The fixed-side member 121 is provided in the fixed state with respect to the cylindrical case 25 of the handle unit 4. Therefore, when the treatment unit 3 and the movable-side member 122 rotate in the periaxial directions integrally with the rotating operation knob 29, the fixed-side member 121, the second suction tube member 83, and the second liquid supply tube member 93 do not rotate. Therefore, when the treatment unit 3 rotates in the periaxial directions, the second suction tube member 83 and the second liquid supply tube member 93 can be effectively prevented from winding around the outer peripheral portion of the sheath portion 31.

Additionally, in the ultrasonic treatment device 1, since the fixed-side member 121 to which the second suction tube member 83 and the second liquid supply tube member 93 are connected does not rotate, the rotation range of the treatment unit 3 does not have to be restricted to 360° or below. Therefore, the rotation regulating portion 110 configured to regulate the rotation range of the rotating operation knob 29 in the periaxial directions with respect to the cylindrical case 25 does not have to be provided between the cylindrical case 25 and the rotating operation knob 29. Therefore, the configuration between the cylindrical case 25 and the rotating operation knob 29 can be simplified.

Modification of Second Embodiment

It is to be noted that the suction intermediate path 130A and the liquid supply intermediate path 130B are not restricted to the configuration according to the second embodiment. That is, the fixed-side member 121 and the movable-side member 122 may cooperatively define the suction intermediate path 130A so that the first suction path 50A and the second suction path 80A communicate with each other irrespective of the state of rotation of the movable-side member 122 with respect to the fixed-side member 121. Further, the fixed-side member 121 and the movable-side member 122 may cooperatively define the liquid supply intermediate path 130B so that the first liquid supply path 50B and the second liquid supply path 80B communicate with each other irrespective of the state of rotation of the movable-side member 122 with respect to the fixed-side member 121.

Other characteristic technical matters of the present invention are added as follows.

Additional Notes (Additional Note 1)

An ultrasonic treatment device comprising:

a handle unit which includes a cylindrical case extended along a longitudinal axis, a fixed handle extended from the cylindrical case toward a handle extending direction that is not parallel to the longitudinal axis, and a movable handle which is pivotably attached to the cylindrical case and which is openable/closable with respect to the fixed handle;

a vibrator unit which includes an ultrasonic vibrator configured to generate ultrasonic vibration, and which is coupled with the cylindrical case from a proximal direction side;

a treatment unit which is coupled with the cylindrical case from a distal direction side, and which is coupled with the vibrator unit in a first coupling region in the cylindrical case, the treatment unit including a probe which is extended from an inside of the cylindrical case to a part to the distal direction side of a distal end of the handle unit along the longitudinal axis and which is configured to transmit the ultrasonic vibration generated by the ultrasonic vibrator from a proximal end to a distal end thereof, and a sheath portion through which the probe is inserted in a state that the probe protrudes toward the distal direction;

a first path defining portion which defines a first path that is opened at an opening position at a distal end of the sheath portion, the first path defining portion being extended to a bending position located to the distal direction side of the first coupling region between the probe and the sheath portion along the longitudinal axis, and being extended to an outside of the treatment unit from an outer peripheral portion of the probe by bending at the bending position; and a second path defining portion which defines a second path communicating with the first path outside the treatment unit, the second path defining portion being extended in the fixed handle of the handle unit from the outside of the treatment unit along the handle extending direction, and being extended to the outside of the handle unit from an extending position located on a handle extending direction side part of the fixed handle.

(Additional Note 2)

The ultrasonic treatment device according to Additional Note 1, wherein the first path defining portion includes a first tube member which is extended to the bending position between the probe and the sheath portion along the longitudinal axis, and which is extended to the outside of the treatment unit from the bending position, and the second path defining portion includes a second tube member which is connected to the first tube member directly or through another member, and which is extended in the fixed handle along the handle extending direction.

(Additional Note 3)

The ultrasonic treatment device according to Additional Note 2, wherein the handle unit includes a rotating operation section which is coupled to the distal direction side of the cylindrical case to be rotatable in periaxial directions with respect to the cylindrical case, and which is configured to rotate the treatment unit with respect to the cylindrical case in the periaxial directions by rotating with respect to the cylindrical case.

(Additional Note 4)

The ultrasonic treatment device according to Additional Note 3, wherein the treatment unit includes a jaw which is pivotably attached to a distal end portion of the sheath portion, and which is openable/closable with respect to a distal end portion of the probe, and the sheath portion includes a movable portion which is coupled with the movable handle in a second coupling region in the cylindrical case located to the distal direction side of the first coupling region, and which is configured to open or close the jaw with respect to the distal end portion of the probe by moving with respect to the handle unit and the probe along the longitudinal axis in accordance with opening/closing motions of the movable handle with respect to the fixed handle.

(Additional Note 5)

The ultrasonic treatment device according to Additional Note 4, wherein the handle unit includes a rotation regulating portion which is provided between the cylindrical case and the rotating operation section, and which is configured to regulate a rotation range of the rotating operation section in the periaxial directions with respect to the cylindrical case to 360° or below, the probe includes a cavity forming portion which is provided between the first coupling region and the second coupling region along the longitudinal axis with having a dimension larger than a half wavelength of the ultrasonic vibration, and which forms a cavity portion that allows connecting the first tube member to the second tube member between the first coupling region and the second coupling region in the cylindrical case, and the first tube member bent at the bending position is extended to the cavity portion from an outer peripheral portion of the cavity forming portion.

(Additional Note 6)

The ultrasonic treatment device according to Additional Note 5, wherein the second tube member is directly connected to the first tube member in the cavity portion.

(Additional Note 7)

The ultrasonic treatment device according to Additional Note 5, wherein the second tube member has a rigidity lower than that of the first tube member.

(Additional Note 8)

The ultrasonic treatment device according to Additional Note 3, further comprising an intermediate path defining portion which defines an intermediate path that intermediates between the first path and the second path, and which connects the first tube member to the second tube member, wherein the intermediate path defining portion includes a fixed-side member to which the second tube member is connected and which is provided to be fixed to the cylindrical case, and a movable-side member to which the first tube member is connected and which is rotatable with respect to the fixed-side member and the cylindrical case in the periaxial directions integrally with the treatment unit, and the movable-side member cooperating with the fixed-side member to define the intermediate path so that the first path communicates with the second path irrespective of a state of rotation of the movable-side member with respect to the fixed-side member.

(Additional Note 9)

The ultrasonic treatment device according to Additional Note 2, wherein the second path defining portion includes an external tube which is connected to the second tube at the extending position, and which is extended to the outside of the handle unit.

(Additional Note 10)

The ultrasonic treatment device according to Additional Note 1, wherein the bending position of the first path defining portion is placed at a node position of the ultrasonic vibration.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment device comprising:
a handle unit including a cylindrical case which is extended along a longitudinal axis, a fixed handle which is extended from the cylindrical case toward a handle extending direction that is a direction crossing the longitudinal axis, a movable handle which is pivotably attached to the cylindrical case, and which is openable and closable with respect to the fixed handle, and an internal space being formed inside the handle unit, the internal space opening with respect to an outside of the handle unit at an opening;

a vibrator unit which includes a vibrator case coupled to a proximal direction side of the cylindrical case, and an ultrasonic vibrator provided at an inside of the vibrator case and configured to generate ultrasonic vibration;

a probe which extends from the internal space of the handle unit toward a distal direction, and which is configured to transmit the ultrasonic vibration generated by the ultrasonic vibrator from a proximal end to a distal end of the probe, a hole-shaped portion being formed at an inside of the probe, the hole-shaped portion being opened with respect to an outside of the probe at a first opening position and a second opening position, the first opening position being placed at the distal end of the probe, the second opening position being placed at an outer peripheral portion of the probe and located inside the cylindrical case in the internal space of the handle unit, the second opening position being placed at a node position of the ultrasonic vibration, and the first opening position and the second opening position communicating with each other via the hole-shaped portion;

a jaw which is configured to open or close with respect to the distal end portion of the probe by opening or closing the movable handle with respect to the fixed handle; and a path which is extended in the hole-shaped portion from the first opening position to the second opening position along the longitudinal axis, and which is extended to the outside of the probe from the second opening position at an inside of the cylindrical case in the internal space of the handle unit, the path being extended from the second opening position to the opening of the handle unit through only the internal space of the handle unit, and the path being extended to the outside of the handle unit from the opening of the handle unit.

2. The ultrasonic treatment device according to claim 1, further comprising a rotating operation section which is coupled with the cylindrical case to be rotatable in directions around the longitudinal axis, and which is configured to rotate the probe, a sheath portion, and the jaw with respect to the cylindrical case in one of the directions around the longitudinal axis with respect to the cylindrical case by a rotation of the rotating operation section.

3. The ultrasonic treatment device according to claim 2, further comprising a movable portion which is provided to an outer peripheral direction side of the probe, and which is configured to open and close the jaw with respect to the distal end portion of the probe by moving with respect to the cylindrical case and the probe along the longitudinal axis in accordance with opening and closing motions of the movable handle.

4. The ultrasonic treatment device according to claim 3, further comprising a rotation regulating portion which is configured to regulate a rotation range of the rotating operation section with respect to the cylindrical case in the directions around the longitudinal axis to 360° or below, wherein the probe has a dimension larger than a half wavelength of the ultrasonic vibration along the longitudinal axis between a first coupling region and a second coupling region, the probe and the movable portion being attached to the vibrator unit in the first coupling region at the inside of the cylindrical case, and the movable handle being coupled with the movable portion in the second coupling region at the inside of the cylindrical case, and the second opening position is placed between the first coupling region and the second coupling region in directions parallel to the longitudinal axis.

5. The ultrasonic treatment device according to claim 2, wherein the rotating operation section is coupled to the distal direction side of the cylindrical case, and the second opening position of the hole-shaped portion is located proximally of the rotating operation section at the inside of the cylindrical case.

6. The ultrasonic treatment device according to claim 1, further comprising:

a first tube member which defines part of the path, and which is extended toward the second opening position in the hole-shaped portion along the longitudinal axis, the first tube member being extended to the outside of the probe from the second opening position; and a second tube member which defines part of the path, and which is connected to the first tube member outside the probe in the internal space of the handle unit, the second tube member being extended through an inside of the fixed handle toward the handle extending direction, wherein the second tube member has a rigidity lower than that of the first tube member.

7. The ultrasonic treatment device according to claim 1, wherein the opening of the handle unit is located at the fixed handle, and the path is extended through the inside of the cylindrical case and an inside of the fixed handle toward the handle extending direction in the internal space of the handle unit.

8. The ultrasonic treatment device according to claim 1, further comprising:

a sheath portion which extends along the longitudinal axis and which is coupled to the distal direction side of the cylindrical case, a proximal end portion of the sheath portion being inserted into the internal space of the handle unit, the probe being extended through an inside of the sheath portion, the distal end portion of the probe protruding from a distal end of the sheath portion toward the distal direction, the jaw being attached to a distal end portion of the sheath portion.

* * * * *